United States Patent [19]

Milani et al.

[11] Patent Number: 4,457,931
[45] Date of Patent: Jul. 3, 1984

[54] PIPERAZINE DERIVATIVES WITH ANTICHOLINERGIC AND/OR ANTIHISTAMINIC ACTIVITY

[75] Inventors: Carlo Milani; Giovanni M. Carminati; Attilio Sovera, all of Italy

[73] Assignee: Selvi & C. S.p.A., Milan, Italy

[21] Appl. No.: 424,512

[22] Filed: Sep. 27, 1982

[51] Int. Cl.³ .................. A61K 31/495; C07D 401/00; C07D 413/00

[52] U.S. Cl. .................. 424/250; 260/243.3; 424/248.4; 544/121; 544/360

[58] Field of Search ............... 544/360, 402, 392, 364; 424/250; 260/243.3

[56] References Cited

FOREIGN PATENT DOCUMENTS 54-103893  8/1979  Japan ................................. 544/360
57-61149   9/1982  Japan ................................. 544/360

OTHER PUBLICATIONS

Bernstein (Squibb), Chem. Abst., vol. 73, (1970), p. 379, 77294p, Adamantane Derivatives, Having Depressant and Antihistaminic Activity.

Frech Squibb, Chem Abst., vol. 74, (1971), p. 603, 141906q, Adamantyl Dibenzoxazepines as Antihistaminic, Antiparkinsonism, Tranquilizing, and Sedative Agents.

Primary Examiner—Donald G. Daus
Assistant Examiner—Cecilia Shen
Attorney, Agent, or Firm—Bucknam and Archer

[57] ABSTRACT

Compounds of formula I

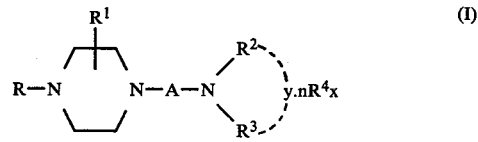

are described in which R is an aryl, substituted aryl, aralkyl or heterocyclic radical; $R^1$ is hydrogen or alkyl of 1–4 carbon atoms; A is a saturated, aliphatic hydrocarbon chain, which is linear or branched; $R^2$ and $R^3$ are the same or different and are hydrogen, linear or branched alkyl, aryl, substituted aryl or together with the nitrogen atom to which they are connected and together with y form a ring wherein y is a methylene group or a heteroatom, which is selected from the group consisting of nitrogen, oxygen and sulfur; $R^4$ is hydrogen or linear or branched alkyl; X is halogen or an organic or inorganic anion; n is 0; 1; 2; 3 or in the case of a bifunctional acid, n is equal to 0.5; 1.5; 2.5 and their enantiomers and diestereoisomers. Several methods of preparation of the novel compounds are described.

18 Claims, No Drawings

PIPERAZINE DERIVATIVES WITH ANTICHOLINERGIC AND/OR ANTIHISTAMINIC ACTIVITY

The present invention relates to piperazine derivatives and more specifically to compounds of general formula I:

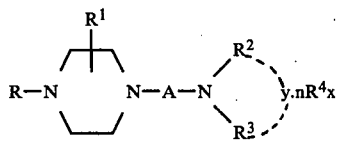

in which:

R is an aryl, substituted aryl, aralkyl or heterocyclic radical;

$R^1$ is hydrogen or $C_1-C_4$ alkyl;

A is a saturated, aliphatic linear or branched chain with at least one or more carbon atoms;

$R^2$ and $R^3$ may be the same or different and are hydrogen, linear or branched alkyl, aryl, substituted aryl or together with the nitrogen atom to which they are connected and together with Y form a ring in which Y is a methylene group or a heteroatom which is N, oxygen or sulfur;

$R^4$ is hydrogen or linear or branched $C_1-C_4$ alkyl;

X is halogen or the anion of an organic or inorganic acid;

n is an integer number equal to 0, 1, 2, or 3 or in the case of bifunctional acids, n is also 0.5, 1.5 and 2.5.

The invention also relates to the enantiomers and/or diestereoisomers of compounds of formula I which contain one or more asymmetric carbon atoms.

Within the scope of the invention are also the methods of preparation of the compounds of formula I which are obtained by several synthetic routes, as it will appear from the examples and as it is summarized in Table I. With respect to the compounds which have asymmetric carbon atoms in the aliphatic chain A, the resolution of the enantiomers is carried out according to classical methods of organic chemistry. The examples of the compounds of formula I which are summarized in Table 2 serve to better illustrate the general concept of the invention without in any way limiting the scope of protection.

Within the scope of the invention are also the pharmacological properties of the compounds of formula I, which consist essentially of a marked spasmolytic anticholinergic activity, as well as therapeutic activity of the substances, which are all the activities resulting from anticholinergic activity, that is among others, gastric antisecretion activity, gastro-intestinal spasmolytic activity, biliary renal, urethral and vesical, mydriatic activity for instillation into the conjuntival sac, antiperkinetic and antikinetosic activity.

By way of example, the results of the pharmacological tests to which have been subjected the products of formula I have been obtained by means of in vitro and in vivo tests. As it appears from Table 3 which summarizes the tests of the compounds according to the present invention, a good part of the activity becomes apparent from the tests in vitro with respect to the spasms induced on the isolated intestine of guinea pigs by acetylcholine in the amount of 0.01–0.001 mcg/ml of solution of the bath because this test shows a substantial anticholinergic activity. The most active compounds in order of activity are referred to hereinbelow with the numbers 26, 17, and 16. These compounds exhibit a DE50, that is 50% decrease of the spastic contractions resulting from the administration of acetylcholine in the range of 0.001–0.006 mcg/ml of solution. Also, active are the compounds designated by numbers 24, 15, 11, 13, 21 and 10 which exhibit a DE50 of 0.01–0.05 mcg/ml of the bath solution.

Two examples of the anticholinergic activity resulting from the administration of different doses of the compounds of the present invention are reported in Table 4.

Several of the compounds which exhibit anticholinergic activity in vitro have been studied in vivo with respect to the lethal bronchospasm induced in guinea pigs by means of an aerosol of acetylcholine. The test has been carried out with 6–8 guinea pigs per group with an aerosol of 0.8% acetylcholine at one atmosphere of pressure.

As it is shown in Table 3, the substances which, administered to guinea pigs by the oral route, have exhibited the greatest anticholinergic activity in the order of activity, are: Compound No. 26, (DE50=20 mg/kg orally): Compound No. 15 (DE50=40 mg/kg orally), as well as Compound No. 10, (DE50=60 mg/kg orally). The symbol DE50 is the dose required to protect 50% of the animals tested from shock.

Table 5 reports in detail several experiments carried out with Compound No. 26 and 15. As it appears from the table in the in vitro tests, with respect to the spasms induced by histamine on the isolated intestine of guinea pigs, (0.01–0.005 mcg/ml of solution) and in the in vivo tests in guinea pigs on the lethal bronchospasm induced by a aerosol of histamine in the amount of 0.1% in distilled water at a pressure of 0.8 atmospheres with 6–8 guinea pigs per group, some of the compounds according to the present invention have demonstrated a clear antihistaminic activity. The most active compound is Compound 2, which has a DE50, that is a protective dose in 50% of the animals equal to 25 mg/kg. Also, Compound Nos. 7, 8, and 14 have exhibited antihistaminic activity in vivo. It is interesting that the compounds which are active as antihistaminic agents are the compounds which have exhibited lower anticholinergic activity.

In view of the fact that the main activity of the compounds of the present invention is the anticholinergic activity, additional research has been carried out by means of two tests, which are considered specific for a demonstration of the anticholinergic activity, that is contractions in guinea pigs caused by neostigmine, (Carminati, Arch. Int. Pharmacodyn., 147, 323, 1964), and salivation in mice caused by pilocarpine, (Screening Methods in Pharmacol., by R. A. Turner, Acad. Press, 1965, page 137).

With respect to the spasms induced in guinea pigs by intravenous injections of neostigmine, the most active compounds if administered intravenously immediately prior to the administration of the spasmogen, result in the decreasing order of activity as 26, 13, 16, 15 and 17 as it is shown in Table 3, which summarizes the doses of several derivatives which result adequate to block at least for three minutes the spastic contractions due to neostigmine.

With respect to the inhibition of salivation due to pilocarpine injected by the subcutaneous route in mice, the most active substances if administered subcutaneously are in the decreasing order of activity, Compounds 26, 17, 16, and 15 as shown in Table 3 in which are reported the dosages capable of reducing the salivation in 50% of the animals with respect to the control group.

Table 6 summarizes an experiment carried out with Compound No. 26.

In the tests in which the administration of the compounds is carried out by the oral route, Compound No. 26 and Compound No. 17 have shown a significant activity followed by Compound Nos. 15 and 10.

Table 3 also summarizes the value of DL50 of the substances being examined by the oral route and in some cases subcutaneously. The DL50 is the lethal dose in 50% of the mice obtained by administration of different doses of each substance in 8–12 mice per dose.

In general, the compounds according to the present invention exhibit scanty toxicity, particularly when they are administered orally. The examination of the data demonstrates that it is likely that in several instances the weak anticholinergic activity manifested by several of the substances examined, when they are administered by the oral route, for instance, Compound Nos. 16, 20, 24, 6 and 11 must be attributed to poor absorption of these substances by the oral route as shown by the relatively high values of the respective DL50 orally.

For the purpose of determining quantitatively the anticholinergic activity of the substance under examination, a study has been carried out under the same experimental conditions used in the tests of the specific activity of three synthetic spasmolytic substances commonly used in therapy and specifically butylscopolamine bromide, prifinium bromide and oxapium iodide. The results obtained are reported in Table 4 together with the results of the most active substances reported in Table 3. The data in Table 7 show that Compound 26 is a spasmolytic substance of long duration with a therapeutic index, that is ratio DL50/DE50 which, orally by comparison with the salivation induced by pilocarpine in mice is equal to 200. The therapeutic index of butylscopolamine bromide under the same experimental conditions is 33.3. The therapeutic index of prifinium bromide is equal to 17 and the therapeutic index of oxapium iodide is equal to 5.55.

Compound 17 also exhibits a substantial spasmolytic activity, but it appears to be somewhat more toxic, (DL50 orally=35 mg/kg). Compound 16, but particularly Compounds 15 and 10 exhibit a spasmolytic activity which in general, is in the same order of magnitude of the activity of the standard reference compounds mentioned hereinabove.

Also, Compound 11 and Compound 13 finally, when they are injected by the parenteral route, exhibit a good spasmolytic activity.

In addition to the spasmolytic and antihistaminic activity, the substances listed in Table 3 have exhibited in screening tests which have been carried out simultaneously, a moderate activity on the central nervous system of mice in the tests of spontaneous mobility, electroshock, traction and inducement of sleep by association with a non-anaesthetic dose of exobarbital of 40 mg/kg intravenously. The table also shows a moderate analgesic activity in the test of Randall and Selitto and antiinflammatory activity in rats by the test of edema on the paw caused by carrageenin.

Two of the substances according to the present invention have been used in preliminary clinical tests in man and specifically:
Compound 26 which is 1-(2-Pyridyl)-4-(1-methyl-2-(1-adamantylamino)ethyl)piperazine and
Compound 15 which is 1-(2-Pyridyl)-4-(1-methyl-2-hexamethyleniminoethyl)piperazine.

The two substances have been used in those clinical syndromes in which it is conventional to use substances of spasmolytic activity. Thirty individuals have been chosen within the scope of the following pathological symptoms: spasms of the gastro-intestine tract; Gastrointestinal ulcers; spasms and dyskinesia of biliary and urinary organs, cervical spasms during delivery, dysmenorrhea prior to diagnostic intervention on cave organs.

There were excluded from the tests, patients having glaucoma, prostatic hypertrophy with tendency for urinary retention, patients with mechanical stenosis of gastro-intestinal organs, individuals with megacolon, with dynamic ilium, with organic pyloric stenosis and finally patients affected by hyperthyroidism and with hepatic and serious renal cardiocirculatory conditions.

The patients are divided into two groups of fifteen subjects each and are treated by the oral route respectively with Compound No. 26 in the amount of 6–12 mg per day and with Compound No. 15 in the amount of 30–60 mg per day. All the animals as an average are treated for twelve days.

A determination of therapeutic activity is expressed keeping in mind the following considerations; nature of the pain, localization and duration of the pain, period of time before the pain appears and frequency of pain; presence of preliminary symptoms and parallel symptomatology, contraction of striated reflex muscles, vegetated participation and emotive reactions. In particular, the period of time necessary for the disappearance of the manifestation of pain after the administration of the substance has been determined.

The tolerability has been valued on the basis of laboratory tests, specifically hematological data, azotemia, glycemia, sierofunctional hepatic data, urinanalysis, and on the basis of the appearance more or less strong of collateral side effects, such as disturbances of accomodation, vertigo, lethargy, cephalargy, thirst, stypsis, nausea, vomiting, anorexia, palpitations, dysuria, and cutaneous rash. The conclusions at the end of the trial have been favorable in a great number of the patients treated with both experimental substances; in particular it has been possible to note that the remission of the spastic symptomatology is achieved with speed and without side effects on the central nervous system. There are, however, present in some subjects, the phenomena as it had been foreseen of anticholinergic type connected with the type of the substance.

Within the scope of the present invention also fall the pharmaceutical compositions which contain as the active substance a compound of general formula I both as the pure product as well as in the presence of a diluent and/or coating. These pharmaceutical compositions may be utilized for oral administration in the form of compresses, powders, granulates, confections, solutions, suspensions, or elixirs. They may also be administered by the rectal route in the form of suppositories together with inert diluents, lubricants, emulsifying agents, etc. They may be administered also by the parenteral route in an aqueous sterile solution also in the presence of other solvents or inert diluents, which are therapeutically compatible. The injectable forms may also be prepared in a solid sterile form, which is solubilized just prior to use by means of suitable solvents.

Finally, the compounds of general formula I may also be utilized in the form of aqueous solutions with or without other suitable ingredients, which are conventionally used in the pharmaceutical industry for opthalmic use.

Some pharmaceutical compositions are reported hereinbelow by way of examples.

EXAMPLE A

Compresses Containing as the Active Ingredient 1-(2-pyridyl)-4-[1-methyl-2-(1-adamantylamino)ethyl]-piperazine (26)

The preparation of 1,000 compresses containing 2 mg each of active ingredient is carried out according to the following procedure. In a container suitable for mixing powders, there are placed 65.5 grams of mais starch and 75 grams of microgranular cellulose. The substances are well-mixed. There is then added to the mixture, two grams of active material in the form of a fine powder while the entire mass is stirred by mixing until a homogenous dispersion is formed.

The mixture thus obtained is transferred to a kneading device into which are introduced sixty grams of a 10% gelatin solution (weight by volume) in distilled water. Then the material is granulated by passing through a granulating machine provided with a screen made of stainless steel. After the granulate is dried in a dryer by means of an air current adjusted to 60° C., up to a residual humidity ≦1, the granulate is passed through a screen made of stainless steel and 15 grams of magnesium stearate is added to the granulate. The mixture is then stirred until a homogenous mass is obtained. The granulate thus obtained is compressed with a compressing machine provided with flat or curved lobes made of chromium-containing stainless steel, thus preparing compresses of 0.150 grams each. The composition of the compresses is as follows:

| Active Component (26) | 2.0 mg |
| Microgranulated cellulose | 75.0 mg |
| Starch of Mais | 65.5 mg |
| Gelatine | 6.0 mg |
| Magnesium Stearate | 1.5 mg |

Compresses of curved shape may also be subjected to a treatment for coating with gastro-soluble polymers.

EXAMPLE B

Compresses Containing as the Active Component 1-(2-pyridyl)-4-[1-methyl-2-(1-adamantylamino)ethyl]-piperazine (26)

In a device suitable for mixing powders are mixed 2 grams of the active ingredient together with 14.75 grams of microcrystalline cellulose. The mixture is then rendered homogeneous by passing through a screen made of stainless steel. To the mixture there is added 132.75 grams of microcrystalline cellulose and 0.5 grams of magnesium stearate. The mixture is then converted into a homogenized dispersion. The mixture is then compressed utilizing a compressing machine provided with flat or curved lobes made of chromium-containing stainless steel. There are thus obtained, 1,000 compresses of 0.150 grams each the composition of which is as follows:

| Active Component (26) | 2.0 mg |
| Microcrystalline Cellulose | 147.5 mg |
| Magnesium Stearate | 0.5 mg |

The compresses of curved shape may be subjected to a treatment of coating with gastro-soluble polymers.

EXAMPLE C

Compresses Containing as the Active Component 1-(2-pyridyl)-4-(1-methyl-2-hexamethyleniminoethyl)-piperazine (15)

The preparation is carried out in analogy with examples A and B and there are obtained compresses containing 10 mg of active component.

EXAMPLE D

Capsules Containing as the Active Component 1-(2-pyridyl)-4-(1-methyl-2-hexamethyleneminoethyl)-piperazine (15)

In an apparatus for mixing powders are placed 10 grams of the active component, 107 grams of powdered lactose, 1 gram of talc, and 2 grams of magnesium stearate. Lactose in powdered form in the amount of 100 grams is added to the mixture thus obtained and the mixture is again mixed until a homogenous dispersion is obtained. Finally, the mixture thus obtained is divided into capsules made of rigid gelatin No. 1 in the amount of 0.220 grams each, thus obtaining 1,000 capsules of the following composition:

| Active Component (15) | 10.0 mg |
| Lactose | 207.0 mg |
| Talc | 1.0 mg |
| Magnesium Stearate | 2.0 mg |

EXAMPLE E

Suppositories Containing as the Active Component 1-(2-Pyridyl)-4-(1-methyl-2-hexamethyleneiminoethyl)-piperazine (15)

The preparation of 1,000 suppositories is carried out as follows. In a suitable container having a double-bottom provided with a stirrer having variable speed, there are melted at about 70° C., 1.980 kg of glyceride esters of saturated fatty acids. The mixture is then cooled while stirring slowly up to a temperature of 40°-42° C. There is then added 20 grams of active ingredient in the form of a powder which may be finely divided or micronized. The mixture thus obtained is passed through a sieve provided with a screen of stainless steel. Then, the fused mass is placed into suitable containers while maintaining the mixture under moderate stirring at 36°-37° C. The suppositories thus obtained are kept at room temperature for about five minutes, then cooled to 5° C. for about fifteen minutes. There are thus obtained 1,000 suppositories of the following composition

| Active Component (15) | 0.020 g |
| Glyceride Esters of Saturated Fatty Acids | 1.980 g |

EXAMPLE F

Suppositories Containing as the Active Component 1-(Pyridyl)-4-[1-methyl-2-(1-adamantylamino)ethyl]-piperazine (26)

The suppositories are obtained by a procedure similar to the procedure of Example E. The composition is as follows:

| Active Component (26) | 0.004 g |
|---|---|
| Glyceride Esters of Saturated Fatty Acids | 1.996 g |

EXAMPLE G

Injectable Solution Containing as the Active Component 1-(2-pyridyl)-4-(1-methyl-2-hexamethyleniminoethyl)piperazine (15)

The preparation of 1,000 vials is carried out as follows: in a suitable container provided with a stirrer, 10 grams of active material are suspended in 2 liters of water suitable for injection. While stirring, 1 N of hydrochloric acid is added slowly until the material goes into solution. The pH of the solution is then adjusted to 6.6±0.1 by slow addition of sodium bicarbonate. The volume of the solution is brought to 3 liters with a solution of 0.9% (weight by volume) of sodium chloride in water suitable for injection while stirring up to complete homogeneity. The solution thus obtained is filtered through a sterilized filter and then through a membrane of 0.15μ/0.20μ. The solution is then divided in vials which had been previously sterilized by heating at 280° C. for 60 minutes and the solution is then distributed in the vials in the amount of 3 ml each. Finally, the material is sterilized by treatment at 120° C. for fifteen minutes. Each vial contains:

| Active Component | 10.0 mg |
|---|---|
| Sterile Isotonic Solution q.b.a. | 3.0 ml |

EXAMPLE H

Injectable Solution Containing as the Active Component 1-(2-Pyridyl)-4-[1-methyl-2-(1-adamantylamino)ethyl]-piperazine (26)

The method of preparation is the same as in Example G. There are obtained 1,000 vials of the following composition:

| Active Component (26) | 2.0 mg |
|---|---|
| Sterile Isotonic Solution q.b.a. | 3.0 ml |

TABLE 1
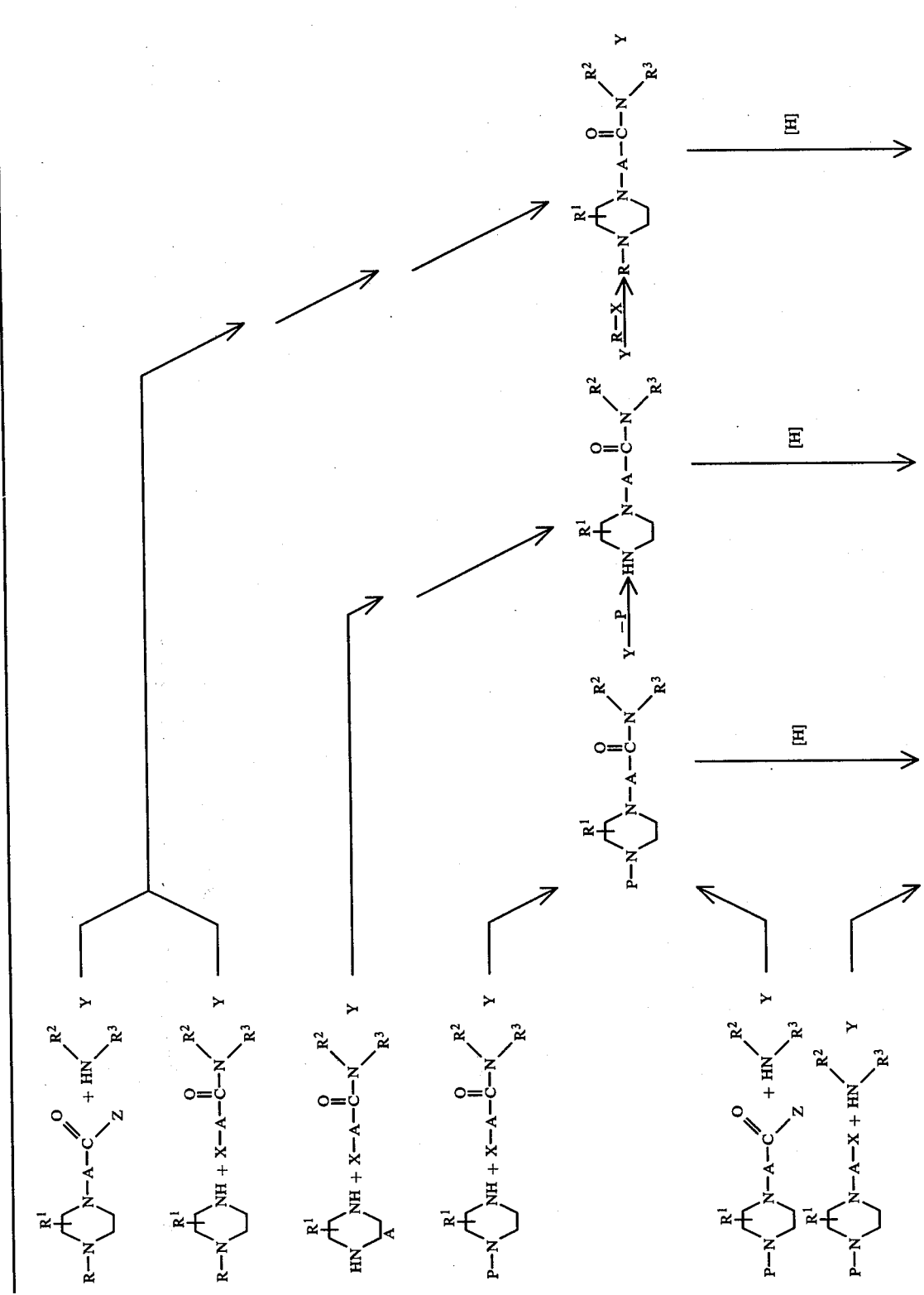

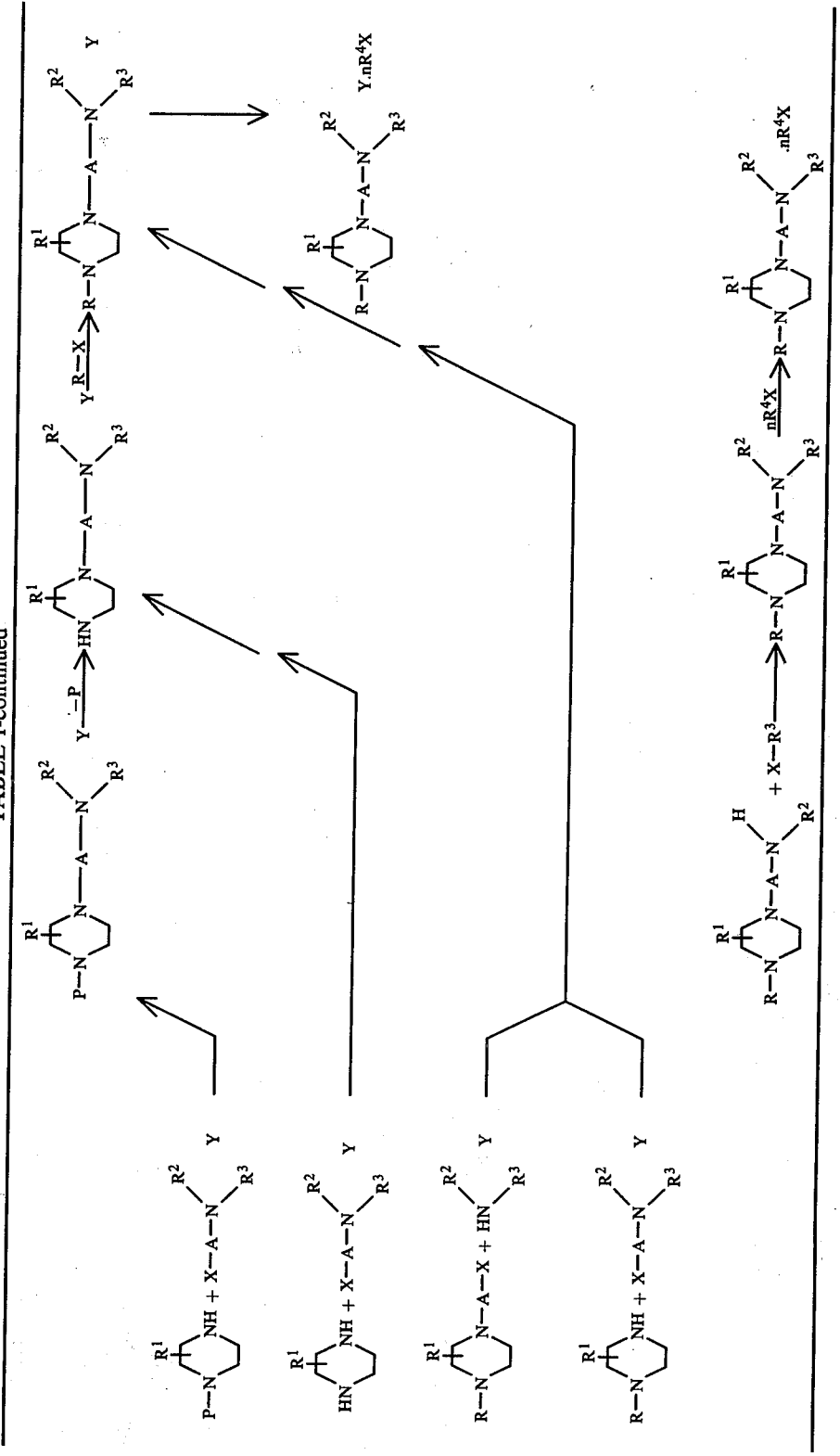

TABLE 2

$$\text{R-N} \underset{\text{R'}}{\overset{}{\bigcirc}} \text{N-A-N} \overset{R^2}{\underset{R^3}{}} \quad Y \cdot nR^4X$$

| n° | Labor. Sigla | R | R' | A | Y | $-N\overset{R^2}{\underset{R^3}{}}$ | n | R⁴ | X | FORMULA | (p.m.) | m.p. °C. (non corr.) | Found % C | H | N | Analysis Calcd % |
|---|---|---|---|---|---|---|---|---|---|---|---|---|---|---|---|---|
| 1 | S.1629 | pyridyl | H | —CH—CH₂— / CH₃ | | —NH / H | 0 | — | — | C₁₂H₂₀N₄ | (220.31) | 89–91 | 65.40 (65.42) | 9.02 (9.15) | 25.39 (25.43) | |
| 2 | S.1581 | pyridyl | H | —CH₂—CH₂— | morpholine | | 0 | — | — | C₁₅H₂₄N₄O | (276.39) | 86–8 | 65.33 (65.18) | 8.66 (8.75) | 20.21 (20.27) | |
| 3 | S.1584 | pyridyl | H | —CH₂—CH₂— | pyrrolidine | | 3 | H | Cl | C₁₅H₂₄N₄·3HCl | (369.79) | 264–6 | 48.66 (48.72) | 7.20 (7.36) | 15.08 (15.15) | |
| 4 | S.1583 | pyridyl | H | —CH₂—CH₂— | piperidine | | 3 | H | Cl | C₁₆H₂₆N₄·3HCl | (383.79) | 289–90 | 50.10 (50.07) | 7.70 (7.62) | 14.57 (14.60) | |
| 5 | S.1564 | pyridyl | H | —CH—CH₂— / CH₃ | morpholine | | 0 | — | — | C₁₆H₂₆N₄O | (290.40) | 58–9 | 66.23 (66.17) | 9.00 (9.02) | 19.32 (19.29) | |
| 6 | S.1589 | pyridyl | H | —CH—CH₂— / CH₃ | morpholine | | 1 | CH₃ | I | C₁₆H₂₆N₄O·CH₃I | (432.37) | 193–5 d. | 47.02 (47.22) | 6.69 (6.76) | 12.88 (12.94) | |

TABLE 2-continued
| n° | Labor. Sigla | R | R' | A | Y | R² R³ | n | R⁴ | X | FORMULA | (p.m.) | m.p. °C. (non corr.) | Found % (Calcd) C | H | N |
|---|---|---|---|---|---|---|---|---|---|---|---|---|---|---|---|
| 7 | S.1580 |  F₃C- | H | -CH₂-CH₂- | -N(C₂H₅)(C₂H₅) | | 2 | H | Cl | C₁₇H₂₆F₃N₃.2HCl | (402.33) | 239-41 | 50.57 (50.75) | 6.93 (7.01) | 10.32 (10.44) |
| 8 | S.1587 | 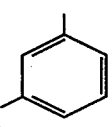 | H | -CH-CH₂- CH₃ |  morpholine | | 0 | — | — | C₁₇H₂₇N₃O | (289.41) | 55-6 | 70.39 (70.55) | 9.40 (9.40) | 14.52 (14.52) |
| 9 | S.1588 | 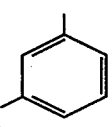 | (2)CH₃ | -CH₂-CH₂- |  morpholine | | 3 | H | Cl | C₁₇H₂₇N₃O.3HCl | (398.82) | 288-90 | 51.33 (51.20) | 7.62 (7.58) | 10.47 (10.51) |
| 10 | S.1566 | 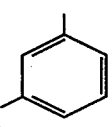 | H | -CH-CH₂- CH₃ |  piperidine | | 0 | — | — | C₁₇H₂₈N₄ | (288.43) | 46-8 | 70.77 (70.79) | 9.80 (9.79) | 19.39 (19.43) |
| 11 | S.1595 | 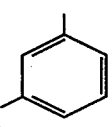 | H | -CH-CH₂- CH₃ |  piperidine | | 1 | CH₃ | I | C₁₇H₂₈N₄.CH₃I | (430.37) | 185-7 | 50.05 (50.23) | 7.30 (7.26) | 12.95 (13.02) |
| 12 | S.1609 | 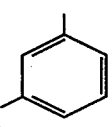 | H | -CH-CH₂- CH₃ |  piperidine | | 2 | CH₃ | I | C₁₇H₂₈N₄.2CH₃I | (572.32) | 230-2 d. | 39.76 (39.87) | 6.05 (5.99) | 9.57 (9.79) |

TABLE 2-continued $$R-N\underset{R'}{\overset{}{\bigcirc}}N-A-N\underset{R^3}{\overset{R^2}{<}} \quad Y.nR^4X$$

| n° | Labor. Sigla | R | R' | A | Y | n | R⁴ | X | FORMULA | (p.m.) | m.p. °C. (non corr.) | Found % (Calcd) C | H | N |
|---|---|---|---|---|---|---|---|---|---|---|---|---|---|---|
| 13 | S.1610 | 2-pyridyl | H | —CH—CH₂—<br>   \|<br>   CH₃ | piperidino | 1 | C₂H₅ | Br | C₁₇H₂₈N₄·C₂H₅Br | (397.40) | 169–72 | 57.55 (57.42) | 8.35 (8.37) | 14.16 (14.09) |
| 14 | S.1603 | 2-pyridyl | H | —CH₂CH₂CH₂— | piperidino | 3 | H | Cl | C₁₇H₂₈N₄·3HCl | (397.82) | 266–8 | 51.02 (51.32) | 8.05 (7.85) | 13.88 (14.06) |
| 15 | S.1604 | 2-pyridyl | H | —CH—CH₂—<br>   \|<br>   CH₃ | hexamethyleneimino | 0 | — | — | C₁₈H₃₀N₄ | (302.45) | 32–3 | 71.25 (71.47) | 9.82 (10.00) | 18.19 (18.53) |
| 16 | S.1602 | 2-pyridyl | H | —CH—CH₂—<br>   \|<br>   CH₃ | hexamethyleneimino | 1 | CH₃ | I | C₁₈H₃₀N₄·CH₃I | (444.40) | 187–9 d. | 51.47 (51.35) | 7.51 (7.48) | 12.44 (12.61) |
| 17 | S.1620 | 2-pyridyl | H | —CH—CH₂—<br>   \|<br>   CH₃ | cyclohexylamino | 2 | H | C₄H₃O₄ | C₁₈H₃₀N₄·2C₄H₄O₄ | (534.60) | 169–71 | 58.16 (58.41) | 7.16 (7.16) | 10.48 (10.48) |

TABLE 2-continued $$R-N\underset{R'}{\overset{}{\bigcirc}}-A-N\underset{R^3}{\overset{R^2}{\diagdown}} \quad Y.nR^4X$$

| n° | Labor. Sigla | R | R' | A | Y | n | R⁴ | X | FORMULA | (p.m.) | m.p. °C. (non corr.) | Found % (Calcd) C | H | N |
|---|---|---|---|---|---|---|---|---|---|---|---|---|---|---|
| 18 | S.1621 | 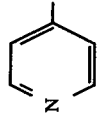 | H | —CH—CH₂— \| CH₃ | 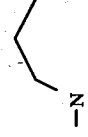 | 1,5 | H | C₄H₃O₄ | C₁₈H₃₀N₄.1.5SC₄H₄O₄ | (476.88) | 105–7 | 60.18 (60.18) | 7.69 (7.61) | 12.00 (11.18) |
| 19 | S.1607 | 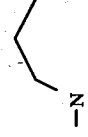 | H | —CH—CH₂— \| CH₃ | —N⟨C₃H₇—i / C₃H₇—i | 0 | — | — | C₁₈H₃₂N₄ | (304.47) | 39–41 | 71.12 (71.00) | 10.48 (10.59) | 18.20 (18.40) |
| 20 | S.1606 | 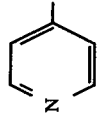 | H | —CH—CH₂— \| CH₃ | —N⟨C₃H₇—i / C₃H₇—i | 1 | CH₃ | I | C₁₈H₃₂N₄CH₃I | (446.42) | 165–7 | 51.03 (51.12) | 7.77 (7.90) | 12.43 (12.55) |
| 21 | S.1613 | 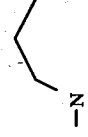 | H | —CH—CH₂— \| CH₃ | —N⟨H / C₆H₁₃—n | 2,5 | H | C₄H₃O₄ | C₁₈H₃₂N₄.2.5 C₄H₄O₄ | (594.64) | 155–7 d. | 56.37 (55.55) | 6.99 (7.12) | 9.69 (9.42) |
| 22 | S.1617 | 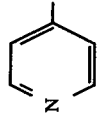 | H | —CH—CH₂— \| CH₃ | 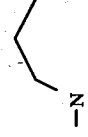 | 0 | — | — | C₁₉H₂₄N₄O₂ | (340.42) | 91–2 | 67.19 (67.03) | 7.10 (7.11) | 16.17 (16.48) |

TABLE 2-continued
$$\underset{R'}{R-N}\overbrace{\phantom{xxxx}}^{} N-A-N\underset{R^3}{\overset{R^2}{<}} \cdot Y.nR^4X$$
| n° | Labor. Sigla | R | R' | A | Y | n | R⁴ | X | FORMULA | (p.m.) | m.p. °C. (non corr.) | Found % C | Analysis Calcd % H | N |
|----|------|---|----|---|---|---|----|---|---------|--------|------|---|---|---|
| 23 | S.1615 | 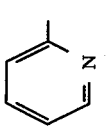 | H | —CH—CH₂— <br> \| <br> C₂H₅ | 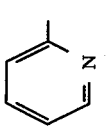 | 3 | H | C₄H₃O₄ | C₁₉H₃₂N₄.3 C₄H₄O₄ | (604.69) | 115–7 d. | 56.14 (56.01) | 6.82 (6.67) | 8.63 (8.43) |
| 24 | S.1616 | 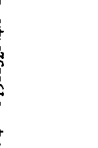 | H | —CH—CH₂— <br> \| <br> C₂H₅ | 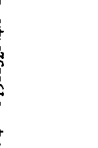 | 1 | CH₃ | I | C₁₉H₃₂N₄.CH₃I | (458.43) | 149–51 d. | 52.02 (52.40) | 7.70 (7.69) | 12.03 (12.22) |
| 25 | S.1632 |  | H | —CH—CH₂— <br> \| <br> CH₃ |  | 3 | H | C₄H₃O₄ | C₂₀H₃₃N₃.3 C₄H₄O₄ | (663.70) | 121–3 | 57.81 (57.90) | 6.88 (6.83) | 6.48 (6.33) |
| 26 | S.1614 | 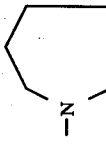 | H | —CH—CH₂— <br> \| <br> CH₃ | 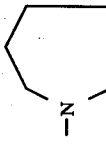 | 0 | — | — | C₂₂H₃₄N₄ | (364.63) | 67–8 | 74.33 (74.53) | 9.82 (9.57) | 15.62 (15.91) |

TABLE 3

Minimum Active Doses (DE50 in mcg/cc or mg/kg) of the Compound of Table 2 in Different Pharmacological Tests

| Compound No. | Sigla | Anticholinergic Activity in vitro (1) | Anticholinergic Activity in vivo (2) Orally | Antihistaminic Activity in vitro (3) | Antihistaminic Activity in vivo (4) Orally | Antispastic Activity on the intestine of guinea pigs i.v. (5) | Activity Against Salivation caused by pilocarpine in mice (6) subcutaneously | Activity Against Salivation caused by pilocarpine in mice (6) orally | DL50 in mice (7) subcutaneously | DL50 in mice (7) orally |
|---|---|---|---|---|---|---|---|---|---|---|
| 1 | S. 1629 | 1.55 | | >20 | | | 40 | | | 700 |
| 2 | S. 1581 | 10 | >50 | 2.5 | 25 | >10 | >50 | | | >1200 |
| 3 | S. 1584 | 2.5 | >50 | 5 | >50 | >10 | >50 | | | 1100 |
| 4 | S. 1583 | 1.8 | >100 | 10 | | >10 | 50 | | | 950 |
| 5 | S. 1564 | 0.35 | 40 | 20 | >60 | 3 | 6 | >30 | | 900 |
| 6 | S. 1589 | 0.3 | | >40 | | | 8 | >100 | | >1200 |
| 7 | S. 1580 | 1 | >50 | 15 | 60 | | | >100 | | 750 |
| 8 | S. 1587 | 3.7 | >60 | 5 | 50 | | 20 | | | |
| 9 | S. 1588 | 60 | | 10 | >50 | | >50 | | | 800 |
| 10 | S. 1566 | 0.052 | 60 | 10 | >60 | 2.5 | 2.3 | 33 | 350 | 350 |
| 11 | S. 1595 | 0.013 | >50 | >50 | | 0.75 | 1.9 | >100 | 200 | >1800 |
| 12 | S. 1609 | 20 | | >20 | | | | | | >1200 |
| 13 | S. 1610 | 0.02 | >50 | >20 | | 0.18 | 1.68 | >100 | | >1200 |
| 14 | S. 1603 | 3.5 | >100 | 10 | 60 | >10 | >10 | | | 450 |
| 15 | S. 1604 | 0.012 | 40 | 15 | >50 | 0.35 | 0.8 | 12 | 225 | 300 |
| 16 | S. 1602 | 0.006 | >50 | >20 | >30 | 0.35 | 0.75 | 65 | 335 | 1100 |
| 17 | S. 1620 | 0.001 | | >20 | | 0.42 | 0.4 | 3 | | 35 |
| 18 | S. 1621 | 1.5 | | >20 | | 10 | >10 | 55 | | 600 |
| 19 | S. 1607 | 0.5 | >50 | 10 | >50 | 2 | >10 | | | 200 |
| 20 | S. 1606 | 1.2 | | >40 | | 2 | 50 | >100 | | >1800 |
| 21 | S. 1613 | 0.02 | | 20 | | 1.3 | 3 | 50 | | 250 |
| 22 | S. 1617 | 1.5 | | | | >10 | 50 | >100 | | 500 |
| 23 | S. 1615 | 0.15 | | >20 | | 1.43 | 15 | 50 | | >250 |
| 24 | S. 1616 | 0.01 | >50 | >20 | | 0.75 | 1.4 | >250 | 380 | >900 |
| 25 | S. 1632 | 0.5 | >100 | >20 | | | >100 | >100 | | 250 |
| 26 | S. 1614 | 0.001 | 20 | 8 | >30 | 0.05 | 0.09 | 1 | 200 | 200 |

(1) Spasms due to acetylcholine in the dose of 0.01–0.001 mcg/cc of solution in the intestine of guinea pigs.
(2) Bronchialspasms caused by an aerosol of acetylcholine in a concentration of 0.8% at one atmosphere in guinea pigs.
(3) Spasms caused by histamine in the dose of 0.01–0.005 mcg/cc of solution in the intestine of guinea pigs.
(4) Bronchialspasms caused by an aerosol of histamine in the concentration of 0.1% at a pressure of 0.8 atmospheres in guinea pigs.
(5) Spastic contractions caused by prostignin in the concentration of 10 mg/kg intravenously in guinea pigs.
(6) Salivation induced by pilocarpine hydrochloride in mice in the dose of 2 mg/kg subcutaneously.
(7) Lethal dose in 50% of the animals in the ten day period subsequent to the treatment by the subcutaneous route and orally.

TABLE 4

Anticholinergic Activity in vitro on the Isolated Intestine of Guinea Pigs of Two of the Compounds under Examination

| Compound No. | Dose in mcg/ml | No. of Tests | Average Decrease in % of the Spasmogenic Effect of Acetylcholine (0.05 mcg/ml of bath) |
|---|---|---|---|
| 26 | 0.00025 | 3 | −5 |
| | 0.00050 | 5 | −34 |
| | 0.00100 | 6 | −50 |
| | 0.00250 | 4 | −76 |
| | 0.00500 | 4 | −91 |
| 16 | 0.00050 | 4 | −16.7 |
| | 0.00100 | 4 | −26 |
| | 0.00250 | 5 | −33 |
| | 0.00500 | 6 | −45 |
| | 0.0100 | 6 | −67 |
| | 0.0250 | 4 | −81 |
| | 0.0500 | 4 | −93 |

TABLE 5

Anticholinergic Activity in vivo with Respect to the Bronchialspasms Caused by Acetylcholine in Guinea Pigs in the Concentration of 0.8% of two of the Compounds being Examined Period of Time in Minutes before the Appearance of the lethal bronchialspasm caused by acetylcholine after the administration of the following

| No. of Animals | Aqua Fontis (controls) 10 cc/kg orally | 15 25 mg/kg orally | 26 20 mg/kg orally |
|---|---|---|---|
| 1 | 102" | 120" | 102" |
| 2 | 77" | >600" | 90" |
| 3 | 40" | 110" | >600" |
| 4 | 90" | >600" | >600" |
| 5 | 53" | >600" | 69" |
| 6 | 44" | 300" | 92" |
| 7 | 90" | 77" | >600" |
| 8 | 102" | 60" | 106" |
| 9 | 61" | 240" | >600" |
| 10 | 81" | 60" | >600" |
| 11 | 65" | 60" | 170" |
| 12 | 40" | 57" | >600" |
| Average time | 71" | >240" | >347.4" |
| No. of animals protected | 0/12 | 3/12 | 6/12 |
| % protection | 0 | 25 | 50 |

TABLE 6

Anticholinergic Activity in vivo with Respect to the Salivation caused by Pilocarpine in the Dose of 2 mg/kg subcutaneously in mice of one compound according to the present invention administered orally one hour prior to pilocarpine.

| | Extension in sq. mm of the area of absorbent paper impregnated with saliva after treatment as indicated below: | | | |
|---|---|---|---|---|
| No. of Animals | Aqua Fontis 10 cc/kg orally (controls) | 26 0.75 mg/kg orally | 26 1.00 mg/kg orally | 26 1.5 mg/kg orally |
| 1 | 322 | 136 | 178 | 10 |
| 2 | 302 | 188 | 130 | 14 |
| 3 | 250 | 202 | 166 | 6 |
| 4 | 314 | 146 | 242 | 10 |
| 5 | 335 | 242 | 202 | 12 |
| 6 | 218 | 168 | 116 | 18 |
| 7 | 384 | 228 | 120 | 36 |
| 8 | 342 | 182 | 168 | 8 |
| 9 | 266 | 212 | 188 | 5 |
| 10 | 274 | 134 | 130 | 22 |
| M | 301 | 184 | 164 | 14 |
| > % | | −38.9 | −45.5 | −95.3 |

Minimum Active Dose (DE50 in mcg/cc or mg/kg of known Anticholinergic Agents and Comparison with Compounds of the Present Invention as listed in the Preceding table in specific Pharmacological Tests

| Substance | Anticholinergic Activity in vitro | Antihistaminic in vitro | Antispastic Activity on the intestine of guinea pigs intravenously | Activity Against Salivation caused by Pilocarpine in Mice | | DL50 of Mice | |
|---|---|---|---|---|---|---|---|
| | | | | subcutaneously | orally | subcutaneously | orally |
| Butylscopoamine bromide | 0.15 | >40 | 1 | 1.3 | 90 | 570 | 3000 |
| Prifinium bromide | 0.003 | 0.5 | 0.2 | 0.15 | 20 | 37 | 340 |
| Oxapium iodide | 0.016 | 1 | 0.75 | 0.3 | 90 | 86 | 500 |
| 26 | 0.001 | 8 | 0.05 | 0.09 | 1 | 200 | 200 |
| 17 | 0.001 | >20 | 0.42 | 0.4 | 3 | | 35 |
| 16 | 0.006 | >20 | 0.35 | 0.75 | 65 | 335 | 1100 |
| 15 | 0.012 | 15 | 0.35 | 0.8 | 12 | 225 | 300 |
| 10 | 0.052 | 10 | 2.5 | 2.3 | 33 | 350 | 350 |
| 11 | 0.013 | >50 | 0.75 | 1.9 | >100 | 200 | >1800 |
| 13 | 0.02 | >20 | 0.18 | 1.68 | >100 | | >1200 |

In the following examples, the melting points have not been corrected. The spectra $^1$H-NMR determined at 60 MHz are tabulated according to the following order: chemical displacement (in δ with respect to TMS), multiplicity (d=duplet, t=triplet, m=multiplet, etc.), constancy of coupling and integration of every signal.

The TLC are performed on plates with silica gel 60 (0.25 mm, F$_{254}$, Merck); the spots after development are determined with U.V. λ254 or 366 nm light or with iodine vapors. The chromatographic columns are prepared, unless differently stated, with 60 silica gel (Merck 70–230 mesh). The numbers in parenthesis after the chemical name refer to the compound as designated in Table 2.

EXAMPLE 1

1-(2-Pyridyl)-4(2-pyrrolidinoethyl)piperazine trihydrochloride (3)

A mixture of 12 grams; (0.074 moles) of 1-(2-pyridyl)-piperazine, 10.2 grams (0.074 moles) of potassium carbonate, and N-(2-chloroethyl)pyrrolidine (10.0 grams; 0.074 moles) in 80 cc xylene is boiled for about 10 hours. After cooling, the mixture is filtered and the filtrate is evaporated under reduced pressure. The oily residue is dissolved in diethyl ether and the solution after cooling is treated with gaseous hydrochloride, thus obtaining the precipitation of the trihydrochloride salt, which is recrystallized until pure: melting point 294°–296° (from methanol); Rf=0.33 (MeOH-conc. NH$_4$OH 97:3); I.R. (nujol), νmax: 2650, 2550, 2420, 2350, 1640, 1610, 1540, 1450, 1440, 1300, 1270, 770 cm$^{-1}$.Cl$^-$ (AgNO$_3$)-calc. % 28.76—Found % 28.85.

1-(2-Pyridyl)-4-(2-piperidinoethy)piperazine trihydrochloride (4)

This substance is obtained in the same manner as described in Example 1, except that the solvent is diethyleneglycoldimethylether and N-(2-chloroethyl)-piperidine is used. The product 1-(2-Pyridyl)-4-(2-piperidinoethyl)piperazine trihydrochloride (4) is obtained with a melting point of 289°–290° (from EtOH-MeOH 1:1); Rf=0.56 (MeOH-Et$_3$N 9:1); I.R. (nujol) νmax: 2460, 2380, 1640, 1625, 1440, 1290, 1135, 975, 760 cm$^{-1}$; Cl$^-$(AgNO$_3$)-calc. % 27.71—Found % 27.61.

1-(2-Pyridyl)-4-(3-piperidinopropyl)piperazine trihydrochloride (14)

The product is obtained according to the procedure of Example 1, but toluene and N-(3-chloropropyl)-piperidine are used. The product, 1-(2-Pyridyl)-4-(3-piperidinopropyl)piperazine trihydrochloride (14) has melting point 266°–268° C. (from MeOH-i-PrOH 1:4); Rf=0.17 (AcOEt-Et$_3$N 9:1); I.R. (nujol) νmax: 2640, 2550, 2460, 1640, 1620, 1290, 770 cm$^{-1}$; $^1$H-NMR (DMSO d-6/D$_2$O 70:30): 1.3–2.6 (m; 8H); 2.6–3.65 (m; 12H); 3.65–4.20 (m; 4H); 6.7–7.37 (m; 2H); 7.70–8.13 (m; 2H).

EXAMPLE 2

1-(2-Pyridyl)-4-(1-methyl-2(3,4-methylenedioxy-phenylamino)ethyl)-piperazine (22)

(a)

N-(3,4-methylenedioxyphenyl)-2-chloropropionamide

To a solution of 3,4-methylenedioxyaniline, (41.1 grams; 0.3 moles) in 270 cc of chloroform containing 90 cc of a 20% solution of sodium hydroxide, there is added 38.1 grams (0.3 moles) of 2-chloropropionyl chloride at about −10° C., while stirring vigorously and keeping the temperature not above −5° C. The mixture is stirred for an additional period of one hour, letting the temperature reach room temperature. The organic phase is then separated, washed with water, neutralized with potassium carbonate and allowed to evaporate at reduced pressure, thus obtaining a solid purplish residue from which the desired product is separated and recrystallized with diisopropyl ether with melting point 116°–117° C.; Rf=0.26 (toluene-AcOEt 9:1) I.R. (nujol) νmax: 3240, 1660, 1540, 1500, 1485, 1445, 1250, 1210, 1040, 930, 815, 790 cm$^{-1}$; chlorine (Schoeninger) calc. % 15.6—Found % 15.5.

(b)
N-(3,4-methylenedioxyphenyl)-2-(4-(2-pyridyl)-1-piperazinyl)propionamide

The amide prepared in part (a) is condensed with 1-(2-pyridyl)-piperazine according to the method used in Example 1, using triethylamine as the base. The desired product is obtained with a melting point of 189°–191° C. (from toluene); Rf=0.44 (AcOEt); IR (nujol) νmax: 3280, 3250, 1680, 1660, 1595, 1540, 1520, 1490, 1450, 1440, 1250, 1165, 1035, 925, 775 cm$^{-1}$.

Elementary Analysis for $C_{19}H_{22}N_4O_3$ (354.40) Calc. %, C=64.39; H=6.26; N=15.81 Found %, C=64.39; H=6.36; N=15.75.

(c) The propionamide prepared according to part (b) is finally reduced with AlLiH$_4$ in THF by the conventional method. The crude reaction product in the form of a dense oil is purified by column chromatography, (petroleum ether-ethyl acetate-triethylamine, 80:10:10), thus obtaining the desired product (22). The melting point is 91°–92° C.; Rf 0.19 (petroleum ether-ethyl acetate Et$_3$N 8:1:1), IR (nujol) νmax: 3340, 3310, 1595, 1500, 1480, 1440, 1315, 1250, 1235, 1210, 1170, 1050, 930, 780 cm$^{-1}$. $^1$H-NMR (CDCl$_3$): 1.03 (d, J=5 Hz; 3H); 2.20–3.13 (m; 7H); 3.30–3.63 (m; 4H); 4.13 (s broadened; 1H); 5.77 (s, 2H); 5.97 (doublet d, J$_1$=8 Hz, J$_2$=2 Hz; 1H); 6.20 (d, J=2 Hz; 1H); 6.33–6.70 (m; 3H); 7.13–7.55 (m; 1H); 8.00–8.20 (m; 1H).

EXAMPLE 3

1-(2-Pyridyl)-4-(2-piperidinoethyl)-piperazine trihydrochloride (4)

(a) N-(2-Piperidinoethyl)piperazine

To a mixture of anhydrous piperazine, 10.0 grams, (0.116 moles) and sodium carbonate (12.3 grams; 0.116 moles) in 70 cc of 1-pentanol brought to the boiling point, is added slowly over a period of four hours, N-(2-chloroethyl)piperidine, (11.3 grams; 0.077 moles) diluted with 150 cc of 1-pentanol. After boiling for an additional period of four hours, the mixture is allowed to cool, it is then filtered and evaporated under reduced pressure. The oily residue is subjected to column chromatography using methanol and concentrated ammonium hydroxide in the ratio of 95:5. The desired product is obtained as an oil, but after standing for a few hours, it solidifies. Melting point is 60°–62° from diisopropyl ether. It forms a picrate: melting point 235°–237° C. (from ethanol); Rf=0.21, (MeOH-NH$_4$OH 9.5:0.5); IR (nujol) max: 3240, 2780, 2760, 1445, 1325, 1300, 1140, 1125, 1105, 865, 770 cm$^{-1}$.

(b) The monosubstituted piperazine prepared in part (a), (7.3 grams; 0.037 moles) is mixed with 2-bromopyridine (5.85 grams; 0.037 moles), in 75 cc of 1-pentanol and in the presence of 4 grams (0.038 moles) of sodium carbonate. After boiling for about ten hours, the mixture is worked up as in Example 1, giving Compound No. 4, identical to the product obtained according to the method described in Example 1. (Melting Point; Mixed Melting Point; Rf; IR).

EXAMPLE 4

1-(2-Pyridyl)-4-(1-methyl-2-(1-adamantylamino)ethyl)-piperazine (26)

(a) Ethyl 2-(4-(2-Pyridyl)-1-piperazinyl)propionate

A mixture of 1-(2-pyridyl)piperazine (15.0 grams; 0.092 moles), ethyl 2-bromopropionate (16.7 grams; 0.092 moles) and potassium carbonate (12.7 grams; 0.092 moles) in absolute ethanol (150 cc) is boiled under reflux for about three hours. After cooling, the mixture is filtered, the filtrate is allowed to evaporate and finally the residue is distilled under vacuo, giving the product, b.p. 130°–132° C. (0.01 mm); Rf=0.37 (from ethyl acetate); IR (neat) νmax: 1730, 1600, 1490, 1440, 1320, 1250, 1160, 985, 780 cm$^{-1}$.

(b)
1-(2-Pyridyl)-4-(2-hydroxy-1-methylethyl)piperazine

A solution of the ester prepared as described above, (15.0 grams; 0.057 moles) in 70 cc of THF is added slowly in an inert atmosphere to a suspension of LiAlH$_4$ (2.2 grams; 0.057 moles) in 150 cc THF. After stirring at room temperature for thirty minutes, the material is decomposed by the usual method and after the conventional work-up, the desired product is obtained, m.p. 62°–64° C. (from diisopropylether); Rf=0.30 (from ethylacetate); IR (nujol) νmax: 3160, 1600, 1560, 1485, 1440, 1315, 1250, 1165, 970, 780 cm$^{-1}$.

(c) 1-(2-Pyridyl)-4-(2-bromo-1-methylethyl)-piperazine

The alcohol prepared in Part (b) hereinabove, (30 grams; 0.136 moles), diluted with 40 ml of chloroform is added dropwise to 15 cc of phosphorus tribromide. The mixture is warmed to about 60° C. for 2 hours. The mixture is then cooled to below 0° C. and the excess of the reagent is decomposed with water. The mixture is made alkaline, the organic phase is separated and the aqueous phase extracted with chloroform. The total organic phase is combined, dried and allowed to evaporate, giving as a residue a yellow solid material, which after recrystallization gives Compound (c) with m.p. 50°–51° C. from n-hexane; Rf=0.54 (from ethyl acetate); IR (nujol) νmax: 1600, 1490, 1445, 1320, 1260, 785 cm$^{-1}$; Br (Schoeninger)—Calculated %: 28.1—Found %: 27.9.

(d) A suspension of 1-adamantylamine (12.0 grams; 0.079 moles) in 250 cc of DMF is prepared. Triethylamine (21.9 cc; 0.158 moles), is added and the mixture is warmed to about 50° C. To the warm solution, there is added over a period of 3 hours, 1-(2-pyridyl)-4-(2-bromo-1-methylethyl)piperazine (18.0 grams; 0.063 moles) keeping the temperature about the same. The reaction mixture is poured into 500 cc of water and then extracted with ether. The ethereal phase, washed with water, then washed to neutrality and allowed to evaporate, gives as a residue, a crude oily product, which is purified by column chromatography. (THF-diisopropyl ether-Et$_3$N 50:40:10). Compound (26) is an oil, which solidifies after prolonged standing; m.p. 67°–68° C. from n-hexane); Rf=0.22 (from ethyl acetate Et$_3$N 9:1); IR (nujol) νmax: 1590, 1480, 1430, 1310, 1240, 1160, 775 cm$^{-1}$; νN-H: 3250 cm$^{-1}$; $^1$H-NMR (CDCl$_3$): 0.93 (d, J=5 Hz; 3H); 1.20–2.23 (m; 16H); 2.23–3.00 (m; 7H);

3.20–3.70 (m; 4H); 6.40–6.73 (m; 2H; 7.23–7.63 (m; 1H); 8.03–8.27 (m; 1H); tripicrate: m.p. 185° C. (from ethanol).

EXAMPLE 5

1-phenyl-4-(2-morpholinoethyl)-2-methylpiperazine (9)

In the same manner as described in Example 1, N-(2-chloroethyl)morpholine is reacted with 1-phenyl-2-methylpiperazine. The trihydrochloride has a melting point 288°–290° (from methanol); Rf=0.63 (MeOH-conc. NH$_4$OH 97:3); IR (nujol) $\nu$max: 2420, 1500, 1405, 1265, 1060, 770, 695 cm$^{-1}$; $^1$H-NMR (D$_2$O; (CH$_3$)$_3$Si(CD$_2$)$_2$ COONa): 1.05 (d, J=6 Hz; 3H; 2.70–4.20 (m; 19H); 7.47 (s; 5H).

EXAMPLE 6

1-(2-pyridyl)-4-(1-methyl-2-hexamethyliminoethyl)piperazine (15)

(a)
N,N-hexamethylene-2-(4-benzylpiperazino)propionamide

To a solution of hexamethylenimine (9.9 grams; 0.1 mole) in toluene, cooled to about 5° C. is added drop by drop, a solution of 2-(4-benzylpiperazino)-propionylchloride (13.3 grams; 0.05 moles). The temperature is allowed to rise, the mixture is then warmed to the boiling point for about 30 minutes. After cooling, the amine hydrochloride is removed and the filtrate is evaporated thus obtaining a gelatinous residue, which is purified by column chromatography, (toluene-methanol 90:10). The product N,N-hexamethylene-2-(4-benzylpiperazino)propionamide has a melting point 79°–80° C. (from diisopropyl ether); Rf=0.28 (toluene-methanol 9:1);

IR (nujol) $\nu$max: 2820, 2800, 2760, 1635, 1430, 1370, 1340, 1290, 1260, 1155, 1140, 1015, 760, 710 cm$^{-1}$.

Calculated for C$_{20}$H$_{31}$N$_3$O: (329.27): Calcd. % Calcd. %: C, 72.90; H 9.48; N 12.75 Found %: C, 73.06; H 9.54; N 12.64.

(b)
N-benzyl-N'-(1-methyl-2-hexamethylimoethyl)piperazine

A solution of the amide prepared as described above (10 grams; 0.03 moles) in 100 cc of toluene is added slowly to a toluene solution of sodium bis-(2-methoxyethoxy)aluminum hydride, (11.2 cc of 70% solution; 0.04 moles). The solution is warmed to boiling, up to complete disappearance of the amide, (by examination with TLC). The product is decomposed with water, filtered, the filtrate is evaporated thus obtaining an oily reddish residue, which is purified by column chromatography, (MeOH-AcOEt-NH$_4$OH 75:22.5:2.5): pale yellow oil with Rf=0.37 (MeOH-AcOEt-NH$_4$OH 75:22.5:2.5); IR (CHCl$_3$) $\nu$max: 2920, 2800, 1490, 1455, 1010, 700 cm$^{-1}$. Trimaleate (25): m.p. 121°–123° C. (from Me$_2$CO); tripicrate: m.p. 187°–191° decomposed from ethanol.

(c) 1-(1-methyl-2-hexamethyleniminoethyl)piperazine

The product is obtained by hydrogenolysis of 1-benzyl-4-(1-methyl-2-hexamethyleniminoethyl)piperazine according to the procedure of R. Boltzly, et al. (Journal American Chemical Society, 66, 263-(1944). The debenzylated product is obtained as a distillable oil: b.p. 99°–102° C. (0.05 mm); Rf=0.15 (MeOH-conc.NH$_4$OH 9.5:0.5); IR (neat) $\nu$max: 2920, 2800, 1450, 1335, 1320, 1170, 1140, 790 cm$^{-1}$; $\nu$NH: 3260 cm$^{-1}$. Dipicrate: m.p. 206°–207° (from ethanol)-

Calcd. for C$_{25}$H$_{33}$N$_9$O$_{14}$ (683.60):
Calcd. %: C,43.92; H,4.87; N,18.44 Found %: C,44.17; H,4.74; N,18.43.

(d) The above prepared monosubstituted piperazine is reacted with 2-bromopyridine in 1-pentanol in the presence of potassium carbonate in analogy with Example 3. The product 1-(2-pyridyl)-4-(1-methyl-2-hexamethyleniminoethyl)-piperazine is purified by means of column chromatography (AcOEt-Et$_3$N 90:10). The pure product has a m.p. 32°–33° C. (from n-hexane); Rf=0.40 (AcOEt-Et$_3$N 9:1); IR (nujol) $\nu$max: 1600, 1565, 1485, 1440, 1315, 1250, 1160, 1140, 980, 770, 730 cm$^{-1}$. $^1$H-NMR (CDCl$_3$): 1.05 (d, J=6 Hz; 3H); 1.60 (s broadened; 8H); 2.15–2.93 (m; 11H); 3.30–3.67 (m; 4H); 6.33–6.70 (m; 2H); 7.20–7.60 (m; 1H); 8.03–8.27 (m; 1H).

EXAMPLE 7

1-(2-Pyridyl)-4-(2-amino-1-methylethyl)piperazine (1)

(a) 2-(4-(2-Pyridyl)-1-piperazinyl)propionamide

The compound, ethyl 2-(4-(2-pyridyl-1-piperazinyl)-propionate obtained as described in Example 4, (15.0 grams; 0.057 moles) dissolved in 30 cc of ethanol is added to 170 cc of an aqueous saturated solution of ammonia and warmed in a sealed stainless steel tube at 100° C. for two days. The reaction mixture is then diluted with water and extracted with ethyl acetate. After the conventional workup, the amide is obtained with m.p. 130°–132° C. (from toluene); Rf=0.1 (ethyl acetate); IR (CHCl$_3$) $\nu$max: 1680, 1600, 1490, 1445, 1390, 1250 cm$^{-1}$; $\nu$-NH$_2$: 3530, 3500, 3420 cm$^{-1}$.

Calcd. for C$_{12}$H$_{18}$N$_4$O (234.30)—Calc. %: C 61.51; H 7.74; N 23.91—Found %: C 61.13; H 7.68; N 23.66.

(b) The amide described hereinabove, reduced with AlLiH$_4$ in ether gives the crude product Compound 1, which is purified by column chromatography (MeOH-concentrated NH$_4$OH 98:2); Rf=0.22 (MeOH-NH$_4$OH 9.8:0.2); IR (neat) $\nu$max: 2820, 1600, 1560, 1485, 1440, 1315, 1250, 980, 775 cm$^{-1}$; $\nu$NH$_2$: 3350, 3280 cm$^{-1}$. The product allowed to stand in the cold for several hours, solidifies; m.p. 89°–91° $^1$H-NMR (CDCl$_3$); 0.70–1.10 (m; 3H); 2.1–3.1 (m; 7H); 3.1–4.1 (m; 6H); 6.33–6.77 (m; 2H); 7.17–7.63 (m; 1H); 7.97–8.27 (m; 1H). Tripicrate: m.p. 223°–226° (dec.); (from ethanol).

EXAMPLE 8

1-(4-Pyridyl)-4-(1-methyl-2-hexamethyleniminoethyl)-piperazine maleate (18)

(a) N,N-hexamethylene-2-(1-piperazinyl)propionamide

N,N-hexamethylene-2-(4-benzylpiperazino)propionamide obtained according to Example 6 is subjected to hydrogenolysis according to the procedure of B. W. Horron (Journal American Chemical Society, 77, 753-(1955). The crude debenzylated product is purified by column chromatography (MeOH-Et$_3$N 95:5). A syrupy oil is obtained which has Rf=0.39 (MeOH-concentrated NH$_4$OH 95:5); IR (neat) $\nu$max: 3300, 2920, 2850, 2820, 1640, 1440, 1370, 1270, 1200, 1165, 1140, 1130 cm$^{-1}$. The dihydrochloride has m.p. 258° C. (dec.) Cl$^-$(AgNO$_3$) calculated %: 23.77—Found: 23.67.

(b) N-(1-methyl-2-hexamethyleniminoethyl)piperazine

The amide described hereinabove (15.7 grams; 0.066 moles) is dissolved in 100 cc of THF and slowly added to a suspension of AlLiH$_4$ (3.8 grams; 0.1 moles) in 50 cc of THF. After boiling for four hours, followed by the conventional workup, a product is obtained which is identical to the product obtained in Example 6, (b.p.; Rf; IR; melting point and mixed melting point of the dipicrate.)

(c) The monosubstituted piperazine described hereinabove is reacted with 4-bromopyridine under the same conditions described in Example 6. The compound 1-(4-pyridyl)-4-(1-methyl-2-hexamethyleniminoethyl)-piperazine, in the crude form is a reddish oil which is purified by column chromatography (MeOH-AcOEt-Et$_3$N 50:40:10) thus obtaining a pale yellow oil: IR (neat) $\nu$max: 2920, 2840, 1600, 1510, 1455, 1395, 1255, 1240, 1150, 995, 810 cm$^{-1}$. $^1$H-NMR (CDCl$_3$): 1.05 (d, J=6 Hz; 3H); 1.57 (s broadened; 8H); 2.0–2.97 (m; 11H); 2.97–3.43 (m; 4H); 6.57 (d, J=6 Hz; 2H); 8.18 (d, J=6 Hz; 2H). The tripicrate has a melting point 196°–198° C. (dec.) (from ethanol).

The base dissolved in ethyl acetate is treated with an equimolar amount of maleic acid, thus giving the maleate salt: m.p. 105°–107° C. (from acetone); Rf=0.41 (AcOEt-MeOH-Et$_3$N, 8:1:1). The mininum molar ratios between the base and the acid are 2:3 (titration with NaOH and HClO$_4$ and elementary analysis).

EXAMPLE 9

1-(2-Pyridyl)-4-(1-methyl-2-hexamethyleniminoethyl)-piperazine methiodide (16)

(a) N,N-hexamethylene-2-(4-(2-pyridyl)piperazino)propionamide

A solution of N,N-hexamethylene-2-(1-piperazinyl)-propionamide (23.9 grams; 0.1 moles) obtained as described in Example 8 in 300 cc of n-butanol is treated with 15.8 grams; 0.1 mole) of 2-bromopyridine in the presence of 13.8 grams of potassium carbonate (1 mole). After boiling up to the elimination of the reactants in TLC (ethyl acetate), the mixture is filtered and the filtrate evaporated, thus obtaining a yellow oily residue, which crystallizes if diluted with petroleum ether: m.p. 110°–111° C. (from diisopropyl ether); Rf=0.16 (AcOEt); IR (nujol) $\nu$max: 1620, 1590, 1480, 1435, 1310, 1250, 1170, 1150, 785 cm$^{-1}$.

Calculated for C$_{18}$H$_{28}$N$_4$O (316.44)—Calculated %: C 68.32; H,8.92; N,17.71—Found %: C,68.15; H,8.77; N,17.65.

(b) The compound prepared as described hereinabove is reduced with AlLiH$_4$ in THF to 1-(2-pyridyl)-4-(1-methyl-2-hexamethyleniminoethyl)piperazine, identical to the product obtained according to the method of Example 6 (melting point; mixed melting point; Rf; IR). This substituted piperazine (7.0 grams; 0.023 moles) dissolved in 50 cc of acetonitrile is treated dropwise with iodomethane, (2.3 grams; 0.023 moles). After about 10 minutes of stirring, the quaternary ammonium salt crystallizes: m.p. 187°–189° C. (dec.) (from ethanol); I$^-$ (AgNO$_3$) calculated %: 28.6—Found %: 28.4; IR (nujol) $\nu$max: 1590, 1480, 1435, 1315, 1250, 780 cm$^{-1}$; $^1$H-NMR (DMSO d-6); 0.96 (d, J=5 Hz; 3H); 1.2–2.2 (m; 8H); 2.2–4.2 (m, 18H); 6.47–6.97 (m; 2H); 7.33–7.70 (m; 1H); 7.97–8.20 (m; 1H).

EXAMPLE 10

1-(2-Pyridyl)-4-(1-methyl-2-piperidinoethyl)piperazine (10)

(a) N-(2-Bromopropionyl)piperidine

Piperidine (73.3 grams; 0.91 moles) is dissolved in 400 cc of toluene and the solution is cooled to −10° C. There is added dropwise, (45.3 cc; 0.45 moles) of 2-bromopropionyl bromide while the temperature is not allowed to exceed −5° C. over a period of three hours. The mixture is stirred again for four hours, while the temperature is allowed to rise, then the mixture is filtered and the filtrate is evaporated under reduced pressure. The product boils at 102° C. (0.3 mm); IR (neat) $\nu$max: 2940, 2860, 1650, 1450, 1380, 1260, 1140, 1020 cm$^{-1}$. The product is a liquid very irritating to the skin and mucosae.

(b) The product described hereinabove is condensed with 1-(2-pyridyl)-piperazine as described in Example 2. There is obtained 2-(N′-(2-pyridyl)piperazinyl)propionylpiperidinamide, which is purified in the form of the dimaleate: m.p. 141°–144° (from Me$_2$CO): Rf=0.65 (CHCl$_3$-MeOH 90:10). This latter compound in the form of a base is reduced with AlLiH$_4$ in THF to 1-(2-pyridyl)-4-(1-methyl-2-piperidinoethyl)piperazine: m.p. 46°–48° C. (from n-hexane); Rf=0.25 (from petroleum ether NEt$_3$ 90:10); IR (nujol) $\nu$max: 2820, 1600, 1490, 1440, 1320, 1255, 1160, 985, 770 cm$^{-1}$; $^1$H-NMR (CDCl$_3$): 1.05 (d, J=6 Hz; 3H); 1.45 (s broadened; 6H); 1.85–3.0 (m; 11H); 3.0–3.7 (m; 4H); 6.37–6.73 (m; 2H); 7.20–7.60 (m; 1H); 8.03–8.23 (m; 1H).

EXAMPLE 11

1-(2-Pyridyl)-4-(1-methyl-2-piperidinoethyl)piperazine methiodide (11)

To a solution of 7.0 grams of 1-(2-pyridyl)-4-(1-methyl-2-piperidinoethyl)piperazine (0.024 moles), prepared as described in Example 10, in 70 cc of acetonitrile, slowly 3.4 grams (0.024 moles) of methyl iodide added. The mixture is stirred for 2½ hours and then let stand at about 2° C. for a few hours during which time crystallization of the quaternary ammonium salt occurs: m.p. 185°–187° C. (from ethanol); I$^-$ (AgNO$_3$)—calculated %: 29.49—Found %: 29.40; IR (nujol) $\nu$max: 1595, 1485, 1440, 1310, 1240, 1170, 975, 775 cm$^{-1}$—$^1$H-NMR (DMSO d-6): 0.95 (d, J=5 Hz; 3H); 1.2–2.2 (m; 6H); 2.2–4.0 (m; 18H); 6.47–6.97 (m; 2H); 7.33–7.67 (m; 1H); 7.97–8.17 (m; 1H).

EXAMPLE 12

1-(2-Pyridyl)-4-(1-methyl-2-piperidinoethyl)piperazine dimethiodide (12)

The compound 1-(2-pyridyl)-4-(1-methyl-2-piperidinoethyl)piperazine (3.0 grams; 0.01 mole), prepared as described in Example 10 is mixed with 2.95 grams (0.021 moles) of methyl iodide and 30 cc of acetonitrile and is heated in a sealed stainless steel tube at 100° C. for 12 hours. After cooling, the liquid is evaporated and the solid is obtained is recrystallized: m.p. 230°–232° C. (dec.) (from methanol); IR (nujol) $\nu$max: 1630, 1570, 1515, 1440, 1250, 1170, 780 cm$^{-1}$.

EXAMPLE 13

1-(2-Pyridyl)-4-(2-piperidinoethyl)piperazine trihydrochloride (4)

(a)

N-(2-Piperidinoethyl)-N'-(ethoxycarbonyl)piperazine

A mixture of 1-ethoxycarbonylpiperazine (10.9 grams; 0.069 moles), N-(2-chloroethyl)piperidine (10.2 grams; 0.069 moles) and potassium carbonate, (9.5 grams; 0.069 moles) in 100 cc of ethanol is heated to reflux for 4 hours. After cooling, the salt is filtered, the filtrate is evaporated and the oily residue is distilled under vacuo; b.p. 133°–136° C. (0.02 mm). Dihydrochloride: m.p. 254°–256° C. (from methanol); Rf=0.74 (MeOH-concentrated NH$_4$OH 9.5:0.5); IR (neat); 2940, 2860, 2820, 1710, 1470, 1435, 1305, 1290, 1240, 1135, 1120, 1005, 770 cm$^{-1}$.

(b) To a solution of potassium hydroxide (6.7 grams) in 60 cc of ethanol, there is added the piperazine compound prepared in Part (a) hereinabove, (10.7 grams; 0.04 moles) and the entire mixture is boiled for about 30 hours. After cooling, the mixture is filtered and the filtrate is concentrated to ⅓ of its volume. After addition of diethylether, a white solid separates, which is collected and recrystallized. The product thus obtained, N-(2-piperidinoethyl)piperazine is identical to the product prepared as described in Example 3, (melting point; mixed melting point; TLC; IR). The product treated with 2-bromopyridine as described in Example 3 gives the trihydrochloride identical to the product obtained according to the method of Example 1 as shown by the melting point, mixed melting point, Rf and IR.

EXAMPLE 14

1-(2-Pyridyl)-4-(2-morpholinoethyl)piperazine (2)

The product is obtained from 1-(2-pyridyl)piperazine according to the procedure described in Example 5. The product is purified by means of column chromatography (C$_6$H$_6$-MeOH 75:25), thus obtaining an oil, which is allowed to stand at room temperature overnight and afterwards it solidifies: m.p. 86°–88° C. (from n-hexane); Rf=0.19 (C$_6$H$_6$-MeOH 75:25); IR (nujol) $\nu$max: 2800, 2780, 1600, 1485, 1440, 1310, 1290, 1250, 1140, 1130, 1110, 1015, 870, 770 cm$^-$; $^1$H-NMR (CDCl$_3$): 2.33–2.73 (m; 12H); 3.33–3.83 (m; 8H); 6.43–6.77 (m; 2H); 7.27–7.67 (m; 1H); 8.10–8.30 (m; 1H).

EXAMPLE 15

1-(2-Pyridyl)-4-(2-amino-1-methylethyl)piperazine (1)

(a) 2-(4-(2-Pyridyl)piperazino)propionitrile

A mixture of 1-(2-pyridyl)piperazine, (18.9 grams; 0.112 moles), potassium carbonate (15.5 grams; 0.112 moles) and 2-chloropropionitrile (10.0 grams; 0.112 moles) in 100 cc of 1-butanol is boiled under reflux for about 9 hours. After cooling, filtering and evaporation of the filtrate, a solid crystalline material is obtained of m.p. 86°–87° C. (from diisopropylether); Rf=0.34 (AcOEt); IR (nujol) $\nu$max: 1600, 1590, 1565, 1485, 1440, 1320, 1260, 1160, 780 cm$^{-1}$; $\nu$-C≡N: 2220 cm$^{-1}$.

Calculated % for C$_{12}$H$_{16}$N$_4$ (216.28): C,66.64; H,7.46; N,25.95—Found %: C,66.61; H,7.44; N,25.87.

(b) The nitrile thus obtained is reduced with AlLiH$_4$ in THF according to the conventional method giving 1-(2-pyridyl)-4-(1-methyl-2-aminoethyl)piperazine, which is identical to the product obtained according to the method of Example 7 as shown by the melting point, mixed melting point, Rf and IR.

EXAMPLE 16

1-(2-Pyridyl)-4-(1-ethyl-2-hexamethyleniminoethyl)piperazine trimaleate (23)

(a) N,N-hexamethylene-2-chlorobutyramide

The product is obtained as an oil by reaction of 2-chlorobutyrylchloride with hexamethylenimine according to the method described in Example 10: b.p. 130°–131° (0.3 mm); Rf=0.44 (AcOEt); IR (neat) $\nu$max: 2920, 2860, 1655, 1440, 1380, 1200, 1175, 910 cm$^{-1}$. Cl (Schoeninger)—Calcd. %: 17.4—Found %: 17.5.

(b)

N,N-hexamethylene-2-(4-(2-pyridyl)-1-piperazinyl)-butyramide

The product described hereinabove is condensed with 1-(2-pyridyl)piperazine in toluene in the presence of Et$_3$N according to the method described in Example 10; m.p. 119°–121° (from diisopropylether); Rf=0.28 (AcOEt); IR (nujol) $\nu$max: 1620, 1595, 1560, 1480, 1440, 1250, 1150, 785 cm$^{-1}$. Calculated % for C$_{19}$H$_{30}$N$_4$O (330.46): C,69.05; H,9.15; N,16.95—Found %: C,69.10; H,9.22; N,16.90.

(c) The butyramide described hereinabove is reduced with AlLiH$_4$ in THF according to the usual method giving Compound 23, which is purified by column chromatography (petroleum ether—Et$_3$N 90:10), thus obtaining a dense pale yellow oil: Rf=0.52 (toluene—Et$_3$N 9:1); IR (neat) $\nu$max: 2920, 2820, 1600, 1560, 1485, 1440, 1385, 1320, 1250, 1165, 1150, 990, 780 cm$^{-1}$—$^1$H-NMR (CDCl$_3$): 0.73–1.13 (m; 3H); 1.13–1.80 (m; 10H); 2.00–3.07 (m; 11H); 3.27–3.60 (m; 4H); 6.33–6.70 (m; 2H); 7.07–7.60 (m; 1H); 8.00–8.27 (m; 1H). By treatment with 3 moles of maleic acid in ethyl acetate, the trimaleate salt is obtained: m.p. 115°–117° C. (dec.) (from ethanol).

EXAMPLE 17

1-(2-Pyridyl)-4-(1-ethyl-2-hexamethylenimoethyl)piperazine methiodide (23)

The compound 1-2(pyridyl)-4-(1-ethyl-2-hexamethyleniminoethyl) is treated with methyl iodide as described in Example 11 and the quaternary ammonium salt is obtained: m.p. 149°–151° C. (dec.) (from EtOH-Et$_2$O). IR (nujol) $\nu$max: 1590, 1480, 1435, 1310, 1245, 1160, 780 cm$^{-1}$: I$^-$ (AgNO$_3$)—Calculated %: 27.7—Found %: 27.9.

EXAMPLE 18

1-(2-Pyridyl)-4-(2-piperidinoethyl)piperazine trihydrochloride (4)

(a) 1-(2-Piperidinoethyl)-4-(ethoxycarbonyl)piperazine

By reaction of 1-(ethoxycarbonyl-4-(2-chloroethyl)-piperazine (11.05 grams; 0.05 moles), piperidine (4.3 grams; 0.05 moles) and potassium carbonate (7.0 grams; 0.05 moles) in 150 cc of ethanol by boiling until disappearance of the reactants by TLC (methanol), a product is obtained which is identical to the product described in Example 13 as shown by boiling point, melting point, mixed melting point of the dihydrochloride; Rf and IR.

(b) By alkaline saponification as described in Example 13 and condensation with 2-bromopyridine according to Example 6 followed by treatment with HCl, the product, the trihydrochloride of 1-(2-pyridyl)-4-(2- piperidinoethyl)piperazine is obtained identical to the product obtained in Example 1 as shown by melting point, mixed melting point, Rf and IR.

EXAMPLE 19

1-(2-Pyridyl)-4-(1-methyl-2-hexamethyleniminoethyl)-piperazine (15)

(a) N,N-hexamethylene-2-(1-piperazinyl)propionamide

To a boiling mixture of anhydrous piperazine (10.0 grams; 0.116 moles) and $Na_2CO_3$ (12.3 grams; 0.116 moles) in 70 cc of 1-pentanol, there is added N,N-hexamethylene-2-chloropropionamide (obtained by reaction of hexamethylenimine and 2-chloropropionyl chloride in analogy with the experiment described in Example 18 in the case of the butyryl homolog; b.p. 103°-104° C. (0.2 mm); Rf=0.56 (AcOEt); Cl (Schoeninger)—calculated %: 18.69; Found %: 18.69; IR (neat); 2920, 2840, 1650, 1450, 1430, 1370, 1190, 1165, 1065, 630 cm$^{-1}$), (14.6 grams; 0.077 moles) dissolved in 150 cc of 1-pentanol. After 4 hours of boiling and subsequent cooling, the salt is filtered off and the filtrate is evaporated. The product so obtained, purified by column chromatography, (MeOH-$Et_3N$ 95:5) is identical to the product obtained according to the method of Example 8 (Rf; IR; melting point, mixed melting point of the dihydrochloride).

(b) N-(1-methyl-2-hexamethyleniminoethyl)piperazine

The amide described above reduced with $AlLiH_4$ in the manner described in Example 8 gives a product similar to that obtained in Example 6, (boiling point; Rf; melting point; mixed melting point of the dipicrate). This monosubstituted piperazine is reacted with 2-bromopyridine in accordance with Example 6 and gives product (15), which is identical to that obtained in the previous example. (melting point; mixed melting point; Rf; IR).

EXAMPLE 20

1-(2-Pyridyl)-4-(1-methyl-2-diisopropylaminoethyl)piperazine (19)

(a) 2-chloropropionic acid diisopropylamide acid

Reaction of 2-chloropropionylchloride with diisopropylamine under the experimental conditions of Example 16, gives the product; b.p. 87°-88° (0.1 mm); Rf=0.67 (methanol); IR (neat) $\nu$max: 2960, 2920, 1650, 1475, 1450, 1370, 1340, 1210, 1040, 620 cm$^{-1}$; Cl (Schoeninger) calculated %: 18.49—Found %: 18.43.

(b) N,N-Diisopropyl-2-(4-2-pyridyl)piperazino)propionamide

The product is prepared from the amide described above by condensation with 1-(2-pyridyl)piperazine according to the method of Example 1: m.p. 101°-104° (from $Et_2O$); Rf=0.29 (AcOEt); IR (nujol); $\nu$max: 1630, 1595, 1480, 1440, 1315, 1290, 1250, 800 cm$^{-1}$. Calculated for $C_{18}H_{30}N_4O$ (318.45): C 67.88; H 9.50; N 17.59—Found %: C, 67.68; H, 9.56; N, 17.60.

(c) The reduction of the above amide with $AlLiH_4$ according to the usual procedure, gives the product 1-(2-pyridyl)-4-(1-methyl-2-diisopropylaminoethyl)piperazine, which is purified by column chromatography, (petroleum ether—$Et_3N$ 90:10): m.p. 39°-41°; Rf=0.62 (petroleum ether—$Et_3N$ 90:10); IR (nujol) $\nu$max: 1595, 1560, 1480, 1440, 1360, 1310, 1250, 1160, 980, 770, 730 cm$^{-1}$; $^1$H-NMR (CDCl$_3$): 0.85-1.17 (m; 15H); 2.13-3.33 (m; 9H); 3.33-3.63 (m; 4H); 6.37-6.67 (m; 2H); 7.20-7.57 (m; 1H); 8.03-8.23 (m; 1H).

EXAMPLE 21

1-(2-Pyridyl)-4-(1-methyl-2-diisopropylaminoethyl)piperazine methiodide (20)

The product obtained according to the preceding example by treatment with methiodide in analogy with Example 9, gives the desired quarternary ammonium salt: m.p. 165°-167° C. (dec.) (from ethanol): I$^-$ (AgNO$_3$)—calculated %: 28.4—Found % 28.6; IR (nujol) $\nu$max: 1600, 1440, 1390, 1365, 1260, 1155, 1050, 785 cm$^{-1}$; $^1$H-NMR (DMSO d-6); 1.00 (d, J=6 Hz; 12H); 1.37 (d, J=5 Hz; 3H); 2.5-4.4 (m; 16H); 6.57-7.03 (m; 2H); 7.40-7.77 (m; 1H); 8.03-8.23 (m; 1H).

EXAMPLE 22

1-(2-Pyridyl)-4-(1-methyl-2-hexamethyleniminoethyl)-piperazine (15)

The compound, N,N-hexamethylenimino-2-chloropropionamide, prepared according to Example 19 is reacted with an equimolar quantity of 1-benzylpiperazine in absolute ethanol in the presence of $K_2CO_3$: N,N-hexamethylene-2-(4-benzylpiperazino)propionamide so obtained is identical to the product obtained according to the method of Example 6 in melting point; mixed melting point; Rf; and IR. This intermediate gives the desired product according to the method of Example 6 or Example 8, but using in the latter case 2-bromopyridine instead of 4-bromopyridine. The product obtained is identical to the product obtained in Example 6 by both procedures, (melting point; mixed melting point; Rf; IR).

EXAMPLE 23

1-(2-Pyridyl)-4-(1-methyl-2-morpholinoethyl)piperazine (5)

(a) 2-bromopropionic acid morpholide

This compound is prepared by reaction of 2-bromopropionylchloride with morpholine under the experimental conditions of Example 10: b.p. 115°-120° C. (0.1-0.2 mm); Rf=0.52 ($C_6H_6$-MeOH 80:20); IR (neat) $\nu$max: 2860, 1660, 1470, 1440, 1280, 1260, 1125, 1040 cm$^{-1}$. The product is very irritating to the skin and mucosae.

(b) 2-(N'-(2-pyridyl)piperazine)propionic acid morpholide

The compound prepared hereinabove in part (a), is condensed with 1-(2-pyridyl)piperazine in benzene and in the presence of triethylamine according to the procedure described in Example 10. The crude product is purified by column chromatography (toluene-methanol 95:5); Rf=0.19 ($C_6H_6$-MeOH 9:1), dimaleate m.p. 150°-152° (from ethanol).

(c) By reduction of the compound prepared in Part (b), with $AlLiH_4$, the desired product is obtained: m.p. 58°-59° C. (from n-hexane); Rf=0.44 (AcOEt-$Et_3N$ 90:10); IR (neat) $\nu$max: 2960, 2850, 2820, 1590, 1480, 1440, 1310, 1250, 1140, 1120, 780 cm$^{-1}$; $^1$H-NMR (CDCl$_3$): 1.05 (d, J=6 Hz; 3H); 1.97-3.13 (m; 11H); 3.13-3.90 (m; 8H); 6.43-6.77 (m; 2H); 7.27-7.63 (m; 1H); 8.07-8.30 (m; 1H).

EXAMPLE 24

1-(2-Pyridyl)-4-(1-methyl-2-morpholinoethyl)piperazine methiodide (6)

The product obtained in Example 23 is treated with equimolar amounts of methyl iodide in acetonitrile at 50° C. for 2 hours. The desired methiodide is obtained; m.p. 193°–195° C. (dec.) (from EtOH-MeOH 2:1); Rf=0.17 (methanol); IR (nujol) $\nu$max: 1590, 1480, 1440, 1320, 1260, 1120, 790 cm$^{-1}$; $^1$H-NMR (DMSO d-6): 0.94 (d, J=5 Hz; 3H); 2.20–4.15 (m; 22H); 6.43–6.93 (m; 2H); 7.30–7.70 (m; 1H); (m; 1H); 7.93–8.17 (m; 1H); I$^-$ (AgNO$_3$) calculated %: 29.35—Found %: 29.16.

EXAMPLE 25

1-(3-Trifluoromethylphenyl)-4-(2-diethylaminoethyl)-piperazine dihydrochloride (7)

The desired product is obtained by reaction of 2-(diethylamino)ethylchloride with 1-($\alpha,\alpha,\alpha$-trifluoro-m-tolyl)piperazine in accordance with the procedure described in Example 1: m.p. 239°–241° C. (from ethanol); Rf=0.74 (n-BuOH-EtOH-AcOH-H$_2$O 40:13.3:26.7:20); IR (nujol) $\nu$max: 2340, 1510, 1490, 1320, 1290, 1270, 1170, 1120, 1090, 950, 790 cm$^{-1}$; $^1$H-NMR (DMSO d-6-D$_2$O 50:50) 1.33 (t, J=7 Hz; 6H); 2.90–3.75 (m; 16H); 6.97–7.67 (m; 4H).

EXAMPLE 26

1-Phenyl-4-(1-methyl-2-morpholinoethyl)piperazine (8)

(a) 2-chloropropionic acid morpholide

The product is obtained by reaction of 2-chloropropionylchloride with morpholine according to the procedure described in Example 23; m.p. 111°–112° C. (1.5 mm); Rf=0.74 (EtOH-concentrated NH$_4$OH 9:1); IR (CHCl$_3$) $\nu$max: 1665, 1470, 1445, 1280, 1260, 1120, 1040 cm$^{-1}$ Cl (Schoeninger)—calculated %: 19.96—Found %: 20.03.

(b) 2-(4-phenylpiperazino)propionic acid morpholide

The compound prepared as described hereinabove is condensed with 1-phenylpiperazine in toluene and in the presence of triethylamine according to the procedure of Example 10; m.p. 105°–107° C. (from diisopropylether); Rf=0.23 (AcOEt-toluene 9:1); IR (nujol) $\nu$max: 1640, 1600, 1430, 1365, 1265, 1245, 1225, 1155, 1140, 1105, 755, 690 cm$^{-1}$.

(c) The reduction of the amide prepared in Part (b) is carried out with AlLiH$_4$. The crude product, 1-phenyl-4-(1-methyl-2-morpholinoethyl)piperazine is purified according to the method of W. C. Still, et al (Journal Organic Chemistry, 43, 2923, 1978); m.p. 55°–56° C.; Rf=0.53 (MeOH-toluene 8:2); IR (nujol) $\nu$max: 1600, 1505, 1300, 1270, 1245, 1140, 1120, 1035, 1015, 970, 780, 760, 690 cm$^{-1}$.

EXAMPLE 27

1-(2-Pyridyl)-4-(1-methyl-2-cyclohexylaminoethyl)piperazine dimaleate (17)

Reactions carried out according to Example 23 have given the following products:

(a) N-cyclohexyl-2-chloropropionamide: b.p. 115°–117° C. (1.2 mm); m.p. 99°–101° C.; Rf=0.40 (toluene-AcOEt); IR (nujol) $\nu$max: 3280, 3080, 1660, 1565, 1230, 1000, 680 cm$^{-1}$; Cl (Schoeninger)—calculated %: 18.7—Found %: 18.7.

(b) N-cyclohexyl-2-(4-(2-pyridyl)-1-piperazinyl)propionamide:

m.p. 126°–128° (from Me$_2$CO); Rf=0.46 (AcOEt-Et$_3$N 9:1); IR (Nujol) $\nu$max: 3270, 1630, 1600, 1565, 1550, 1480, 1440, 1310, 1250, 980, 790 cm$^{-1}$. Calculated % for: C$_{18}$H$_{28}$N$_4$O (316.44)—C 68.32; H 8.92; N 17.71—Found %: C,68.24; H,8.82; N,17.58.

(c) 1-(2-pyridyl)-4-(1-methyl-2-cyclohexylaminoethyl)-piperazine

This substance is purified by column chromatography (pet. ether, CH$_2$Cl$_2$—Et$_3$N (50:40:10). The product is obtained in the form of a thick colorless oil; IR (neat) $\nu$max: 2960, 2920, 2840, 2810, 1595, 1480, 1440, 1310, 1250, 980, 775 cm$^{-1}$. The base so obtained is treated with 2 moles of maleic acid thus giving the dimaleate: m.p. 169°–171° C. (from ethanol); Rf=0.36 (petroleum ether-CH$_2$Cl$_2$-Et$_3$N 5:4:1); $^1$H-NMR (DMSO d-6): 0.75–2.25 (m; 13H); 2.25–3.30 (m; 9H); 3.30–3.70 (m; 4H); 6.13 (s, 4H); 6.47–7.07 (m; 2H); 7.30–7.73 (m; 1H); 7.97–8.20 (m; 1H); 9.75 (s broadened; 4H).

EXAMPLE 28

1-(2-Pyridyl)-4-(1-methyl-2-piperidinoethyl)piperazine methobromide (13)

A mixture of 1-(2-pyridyl)-4-(1-methyl-2-piperidinoethyl)piperazine prepared in accordance with Example 10, (3.0 grams; (0.01 mole), is reacted with 1.2 grams (0.11 mole) of bromoethane in 20 cc of acetonitrile in a sealed tube and warmed at 80°–90° C. for about 3 hours. The solution thus obtained is allowed to evaporate giving a solid, which is repeatedly purified with diethyl ether: m.p. 169°–172° C.; IR (nujol) $\nu$max: 1590, 1560, 1440, 1315, 1240, 980, 780 cm$^{-1}$.

EXAMPLE 29

1-(2-Pyridyl)-4-(1-methyl-2-n-hexylaminoethyl)piperazine maleate (21)

The following products are obtained similarly to Example 23:

(a) N-n-hexyl-2-chloropropionamide: b.p. 105°–105° C. (0.2 mm); m.p. about 16°–17°; IR (neat) $\nu$max: 3280, 2920, 2860, 1660, 1550, 1465, 1460, 1450, 1375, 1220 cm$^{-1}$—Cl (Schoeninger)—calculated %: 18.5—Found %: 18.7.

(b) N-n-hexyl-2-(4-(2-pyridyl)-1-piperazinyl)propionamide

Oily liquid; IR (neat) $\nu$max: 2950, 2920, 2850, 1665, 1600, 1520, 1480, 1440, 1250, 760 cm$^{-1}$; —NH; 3350 cm$^{-1}$—also identified as the dimaleate: m.p. 131°–132° C.; Rf=0.47 (AcOEt-Et$_3$N) 9:1)—Calculated for C$_{26}$H$_{38}$N$_4$O$_9$ (550.60)—C,56.71; H,6.96; N,10.18—Found %: C,56.59; H,6.80; N,10.23.

(c) 1-(2-Pyridyl)-4-(1-methyl-2-n-hexylaminoethyl)piperazine

Purified by means of column chromatography, (AcOEt-petroleum ether-Et$_3$N 50:40:10), the product is obtained in the form of an oil: Rf=0.22 (AcOEt-petroleum ether-Et$_3$N 5:4:1); IR (neat) $\nu$max: 2960, 2920, 2850, 2820, 1600, 1485, 1440, 1320, 1250, 980, 775 cm$^{-1}$ $\nu$-NH: 3300 cm$^{-1}$; $^1$H-NMR (CDCl$_3$): 0.80–1.07

(m; 6H); 1.35 (s broadened; 8H); 2.08 (s; 1H); 2.23–3.10 (m; 9H); 3.33–3.67 (m; 4H); 6.40–6.70 (m; 2H); 7.23–7.60 (m; 1H); 8.05–8.27 (m; 1H). Tripicrate m.p. 167°–169° C. (from ethanol). The base in the amount of 0.01 mole is treated with maleic acid in the amount of 0.03 moles in 5 ethyl acetate thus giving the maleate: m.p. 155°–157° C. (dec.) (from i-PrOH); Rf=0.20 (AcOEt-Et₃N 9:1). On the basis of the titration of the acid with sodium hydroxide and titration of the base with HClO₄ and on the basis of the microanalysis, in this salt, the minimum molar ratios between base and acid are 2:5.

EXAMPLE 30

1-(2-Pyridyl)-4-(1-methyl-2-(1-adamantylamino)ethyl)-piperazine (26) By using the method described in Example 2, the following compounds are obtained:

(a) N-(1-adamantyl)-2-chloropropionamide:

m.p. 99°–100° C. (from n-hexane); Rf=0.56 (petroleum ether-AcOEt 6:4); IR (nujol) νmax: 3280, 3070, 1660, 1560, 1450, 1360, 1220, 1070 cm⁻¹. —Cl (Schoeninger) calculated %: 14.67—Found %: 14.70.

(b) N-(1-adamantyl)-2-(4-pyridyl)piperazino)propionamide purified by column chromatography (ethyl acetate): m.p. 137°–139° C.; Rf=0.35 (AcOEt); IR (nujol) νmax: 3280, 1660, 1600, 1560, 1520, 1440, 1255 cm⁻¹. Calculated for C₂₂H₃₂N₄O: C,71.70; H,8.75; N,15.20—Found %: C,71.59; H,9.00; N,15.06.

(c) 1-(2-pyridyl)-4-(1-methyl-2-(1-adamantylamino)ethyl)-piperazine identical to the product obtained according to Example 4, (melting point; mixed melting point; Rf; IR).

EXAMPLE 31

1-(2-Pyridyl)-4-{1-methyl-2-(1-adamantylamino)ethyl)} piperazine (26)

The product obtained according to Example 15 or 1-(2-pyridyl)-4-(2-amino-1-methylethyl)piperazine, (2.20 grams; 0.01 mole) is condensed with 1-bromoadamantane according to the procedure described by E. V. Krumkalns and W. Pfeifer, (J. Med. Chem. 11, 1103-1968). The crude product so obtained is purified as described in Example 7 and has the same properties of the product obtained according to Examples 7 and 15.

What is claimed is:

1. A compound of formula I

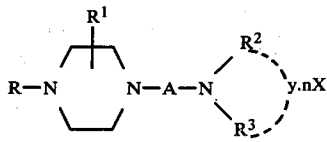

wherein:
R is phenyl, unsubstituted or mono or di substituted by trifluoromethyl; benzyl, 2-pyridyl;
R¹ is hydrogen;
A is a saturated, linear or branched alkylene chain of up to 4 carbon atoms;
R² and R³ are the same or different and are hydrogen, linear or branched alkyl of 2–6 carbon atoms or the group

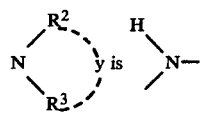

methylene dioxy phenyl when y is zero; or are an alkylene chain which together with the nitrogen atom to which they are connected and together with y form a 5-, 6- or 7-member ring which is a cyclic group having one N atom, adamantyl or cyclohexyl;

X is halogen or a pharmaceutically acceptable organic or inorganic anion;

n is 0; 1; 2; 3 or in the case of a bifunctional acid, n is equal to 0.5; 1.5; 2.5 and lower alkyl quaternary compounds and enantiomers and diestereoisomers thereof.

2. A compound according to claim 1, wherein R is 2-pyridyl and the group

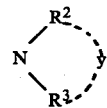

is (a) cyclohexylamino; (b) dialkylamino; (c) adamentylamino; (d) piperidino; (e) hexamethylenimino; or (f)

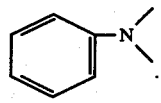

3. A compound according to claim 2, wherein R is 2-pyridyl; R² is H; A is an alkylene chain of up to 4 carbon atoms; and

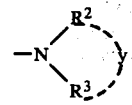

forms the adamantylamino group.

4. A compound according to claim 2, wherein R is 2-pyridyl; R² is H; and the group

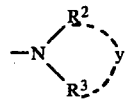

forms the cyclohexylamino group; A is an alkylene chain of up to 4 carbon atoms.

5. A compound according to claim 2, wherein R is 2-pyridyl or benzyl; A is an alkylene chain of up to 4 carbon atoms and

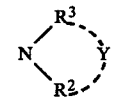

the hexamethylenimino ring.

6. A compound according to claim 2, wherein R is 2-pyridyl; A is an alkylene chain of up to 4 carbon atoms;

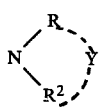

forms the piperidino ring.

7. A compound according to claim 2, wherein R¹ is phenyl substituted by a trifluoromethyl group; A is an alkylene chain of up to 4 carbon atoms; and the group

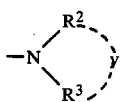

forms a dialkylamino group.

8. The compound according to claim 2, wherein said group

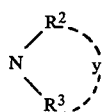

forms the anilino group additionally substituted by a dioxy-methylene group.

9. A compound according to claim 1, which is 1-(2-pyridyl)-4-(2-(1-adamantylamino)-1-methylethyl)piperazine.

10. A compound according to claim 1, which is 1-(2-pyridyl)-4-(1-methyl-2-cyclohexylaminoethyl)piperazine.

11. A compound according to claim 1, which is 1-(2-pyridyl)-4-(1-methyl-2-hexamethyleniminoethyl)piperazine methiodide.

12. A compound according to claim 1, which is 1-(2-pyridyl)-4-(1-methyl-2-hexamethyleniminoethyl)piperazine.

13. A compound according to claim 1, which is 1-(2-pyridyl)-4-(1-methyl-2-piperidinoethyl)piperazine.

14. A compound according to claim 1, which is 1-(2-pyridyl)-4-(1-methyl-2-piperidinoethyl)piperazine methiodide.

15. A compound according to claim 1, which is 1-(2-pyridyl)-4-(1-methyl-2-piperidinoethyl)piperazine ethobromide.

16. A compound according to claim 1, which is 1-(2-pyridyl)-4-(1-ethyl-2-hexamethyleniminoethyl)piperazine methiodide.

17. A compound according to claim 1, which is 1-(2-pyridyl)-4-(1-methyl-2-n-hexylaminoethyl)piperazine maleate.

18. A pharmaceutical composition having anti-cholinergic activity, suitable for administration by the oral, rectal, parenteral route and by eye instillation, which contains as the active component a compound according to claim 1 or a pharmaceutically compatible salt thereof.

* * * * *